(12) United States Patent
Ja

(10) Patent No.: US 7,982,878 B1
(45) Date of Patent: Jul. 19, 2011

(54) OPTICAL EMISSION COLLECTION AND DETECTION DEVICE AND METHOD

(75) Inventor: Shiou-jyh Ja, Stillwater, OK (US)

(73) Assignee: Nomadics, Inc., Stillwater, OK (US)

( * ) Notice: Subject to any disclaimer, the term of this patent is extended or adjusted under 35 U.S.C. 154(b) by 273 days.

(21) Appl. No.: 12/245,574

(22) Filed: Oct. 3, 2008

Related U.S. Application Data

(60) Provisional application No. 60/997,457, filed on Oct. 3, 2007.

(51) Int. Cl.
*G01N 21/55* (2006.01)
*G01N 21/64* (2006.01)

(52) U.S. Cl. ...................................... 356/445; 250/458.1

(58) Field of Classification Search .......... 356/445–448, 356/432–437, 244, 246; 250/461 R, 458.1, 250/336.2
See application file for complete search history.

(56) References Cited

U.S. PATENT DOCUMENTS

| | | | | |
|---|---|---|---|---|
| 4,180,739 A | * | 12/1979 | Abu-Shumays | 250/461.1 |
| 4,818,710 A | * | 4/1989 | Sutherland et al. | 436/527 |
| 5,341,215 A | * | 8/1994 | Seher | 356/445 |
| 5,508,809 A | * | 4/1996 | Peacock et al. | 356/445 |
| 5,747,349 A | * | 5/1998 | van den Engh et al. | 436/172 |
| 6,300,638 B1 | * | 10/2001 | Groger et al. | 250/458.1 |
| 6,339,062 B1 | * | 1/2002 | Williams et al. | 514/13.3 |
| 6,346,376 B1 | * | 2/2002 | Sigrist et al. | 435/5 |
| 6,783,814 B2 | | 8/2004 | Swager | |
| 7,301,642 B2 | * | 11/2007 | Shimizu | 356/445 |
| 7,443,507 B2 | * | 10/2008 | Ran et al. | 356/445 |
| 7,718,964 B2 | * | 5/2010 | Frey | 250/336.2 |
| 7,835,006 B2 | | 11/2010 | Ja | |
| 2005/0053974 A1 | | 3/2005 | Lakowicz et al. | |
| 2006/0109472 A1 | * | 5/2006 | Muraishi | 356/445 |

OTHER PUBLICATIONS

Lakowicz, J. R., "Radiative decay engineering 3. Surface plasmon-coupled directional emission," Analytical Biochemistry, 324, pp. 153, 2004.

Gryczynski, I. et al., "Ultraviolet sruface plasmon-coupled emission using thin aluminum films", Anal. Chem. 2004, 76, 4076, 2004.

* cited by examiner

*Primary Examiner* — Sang Nguyen
(74) *Attorney, Agent, or Firm* — McAfee & Taft

(57) ABSTRACT

This invention generally relates to optical devices that can collect and detect signal emissions effectively while allowing the excitation light path and the sample flow path to coexist non-obstructively in a compact format. More specifically, this invention relates to a compact device having a multilayer coating on the structure surface and a wave guiding structure. In the device, using the surface plasmon coupling effect, the majority of the optical emission from the emitter on top of the multilayer coating is distributed toward the wave guiding structure. The wave guiding structure then further directs the emission signal to the detector with a high efficiency.

25 Claims, 14 Drawing Sheets

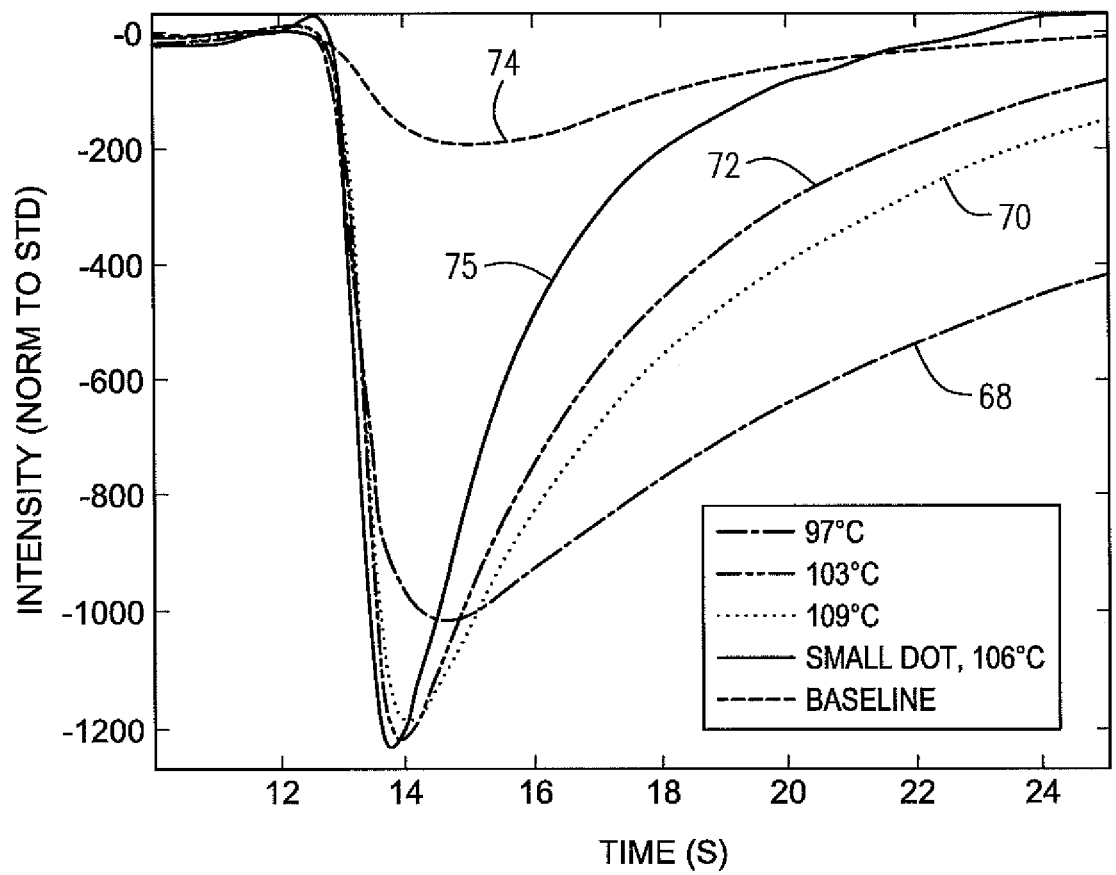
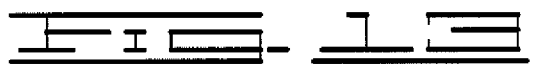

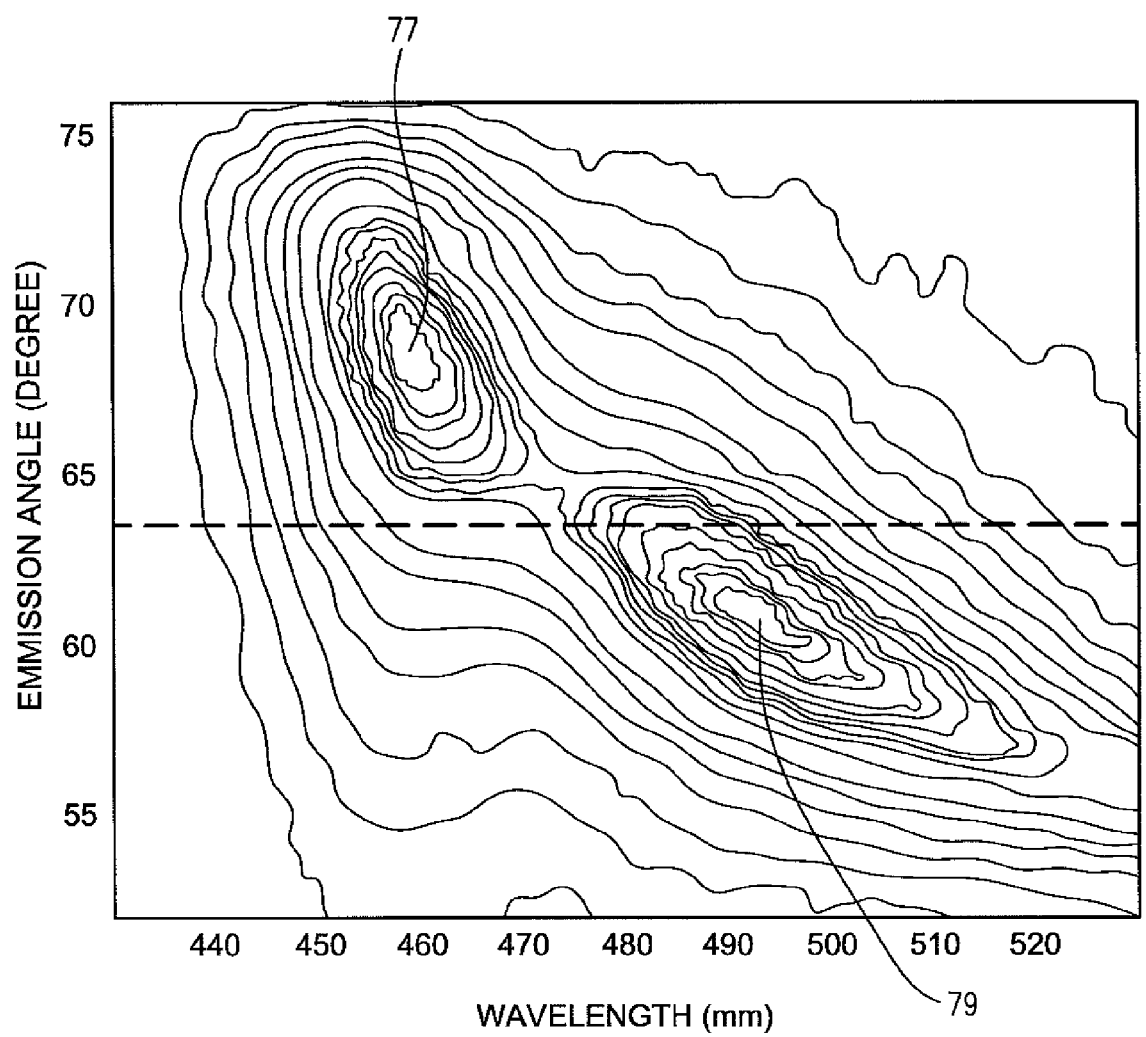

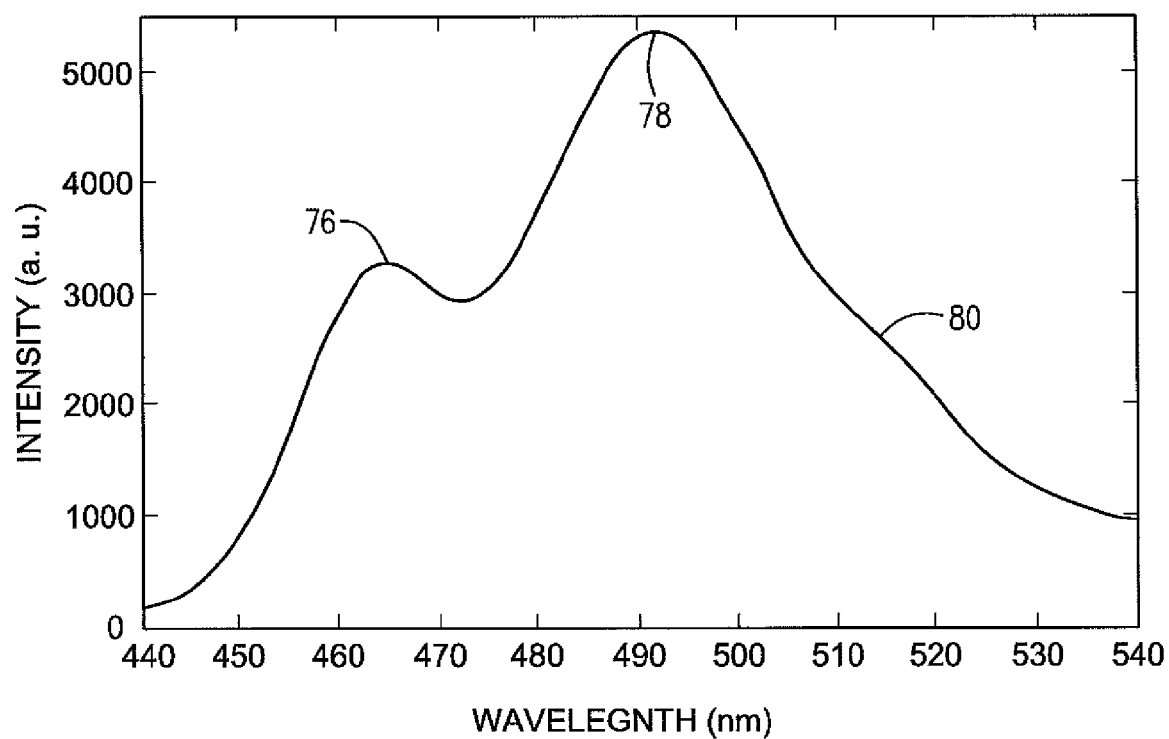
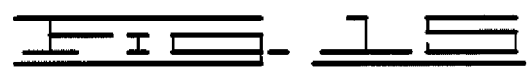

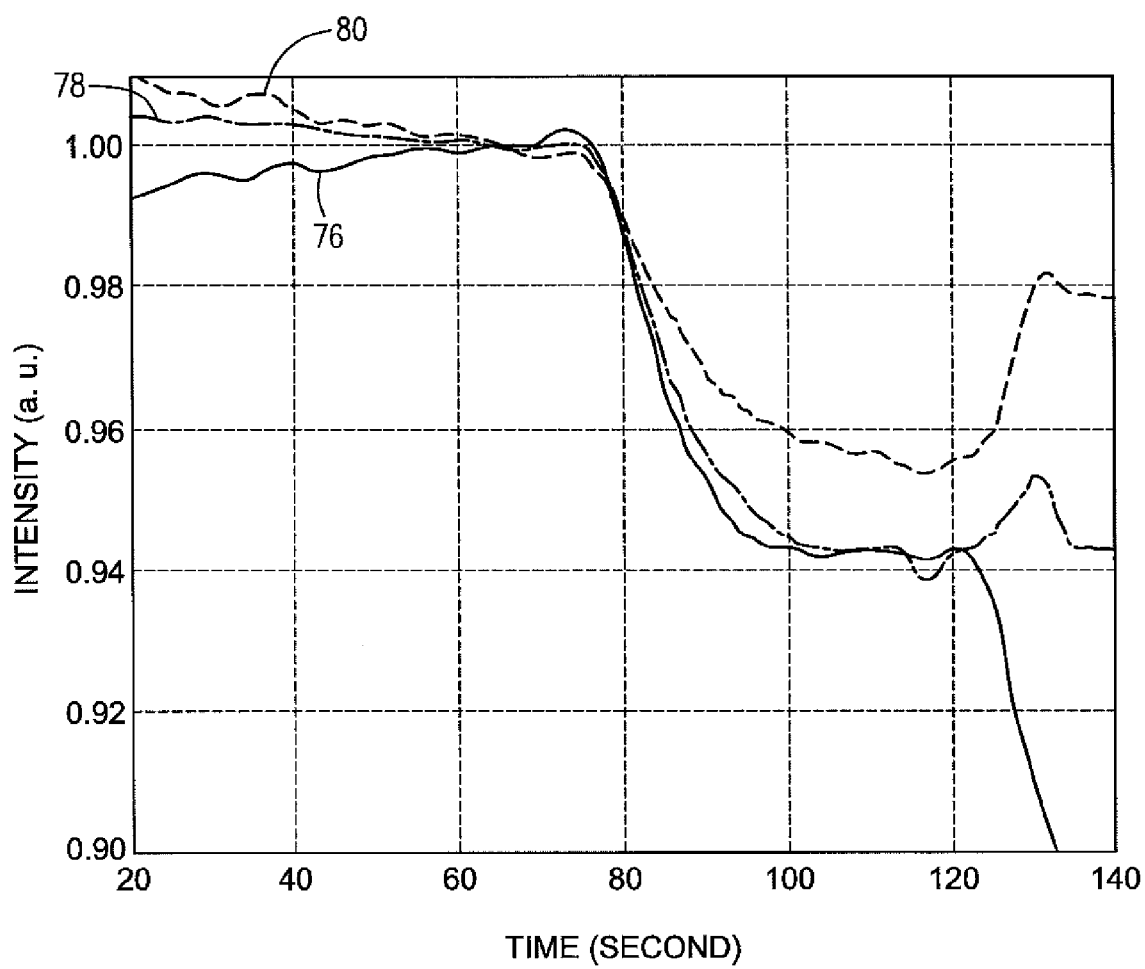
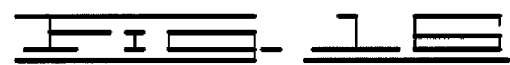

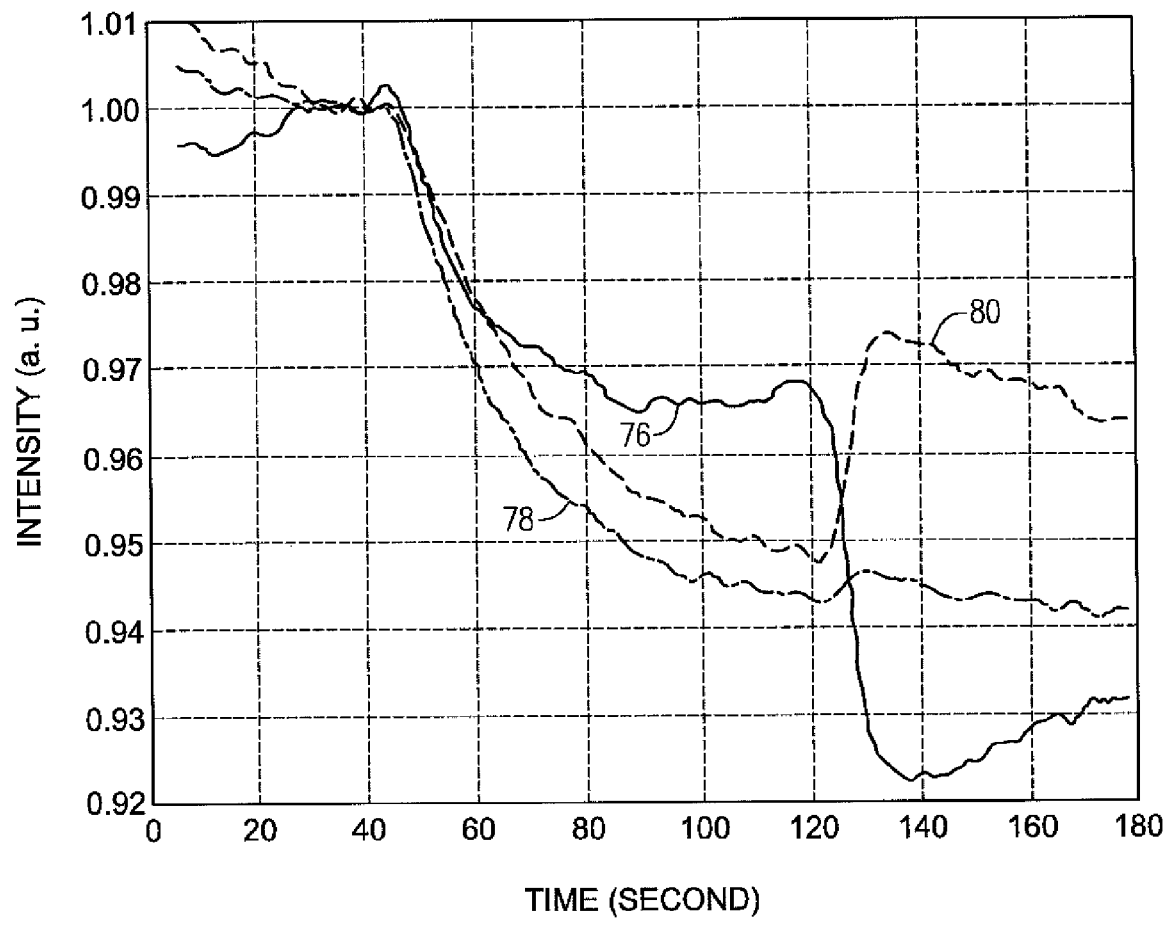

OPTICAL EMISSION COLLECTION AND DETECTION DEVICE AND METHOD

CROSS-REFERENCE TO RELATED APPLICATION

This application claims the benefit of U.S. Provisional application No. 60/997,457, filed Oct. 3, 2007.

STATEMENT AS TO FEDERALLY SPONSORED RESEARCH

This application was supported in part by a contract from the U.S. Department of Defense's Defense Advanced Research Projects Agency (DARPA), Contract Number: W31P4Q-04-C-R308. The United States Government may have rights in, and to, this application by virtue of this funding.

BACKGROUND OF THE INVENTION

The present invention is for a new inventive device and method to collect and detect optical fluorescent emissions from a reporter and an analyte. In particular, the present invention is an optical collection device for collecting fluorescent optical emissions at the molecular level, and a method for using the same. The molecular-based optical fluorescence emission detection system is an optical device suitable for sensing the presence of explosive, chemical or biological warfare substances using a chemical warfare indicating chromophore (CWIC) or amplifying fluorescence polymers (AFPs).

Explosive, chemical and biological substances are difficult to detect. One approach for detecting these substances is to use a fluorescence detection scheme. The explosive, chemical and biological substances, called analytes, interact with an innovative fluorescent material such as a CWIC or AFP, and cause changes in the intensity, wavelength, or the duration of the fluorescence signal. The detection of explosive, chemical or biological substances can be achieved by monitoring such changes. One challenge of traditional fluorescence-based detection systems is the low signal-to-noise ratio (SNR). The low SNR may be due to the low fluorescence signal and the presence of excitation light and ubiquitous background noise in the signal collection path.

One focus of current research is to improve the detection of explosive, chemical and biological warfare substances reacting with CWIC or AFP materials by improving optical collection efficiency and noise rejection. As an alternative to traditional fluorescence-based methods, surface plasmon-coupled emission (SPCE) sensors are best suited to collect fluorescing emissions, and provide increased optical SNR and hence sensitivity. Testing has shown that a SPCE sensor arrangement enhances fluorescence signal strength by significantly improving the collection efficiency. Additionally, a SPCE sensor arrangement increases the signal-to-noise ratio via the implementation of forbidden light detection and polarization filtering. The highly p-polarized SPCE signal allows polarization filtering to be used to further improve signal-to-noise ratio. These two advantages enable high sensitivity and low detection limits for the fluorescence-based detection system. However, current optical collection devices for SPCE sensor arrangements are cumbersome and difficult to use.

The need is for a less cumbersome apparatus and method to optically detect the fluorescent emission from an explosive, chemical or biological warfare substance reacting with a CWIC or AFP while having a high signal-to-noise ratio. The requirement is to have a portable apparatus to detect the fluorescent emissions of explosive, chemical or biological warfare samples generated from the reaction of the samples with CWIC or AFP material.

SUMMARY OF THE INVENTION

In one embodiment, the current invention provides an optical detection device. The optical detection device comprises a housing having an input segment suitable for receiving an analyte transport fluid. Further, an optic segment and a sensing slide are positioned within the housing. The sensing slide carries at least one reporter having the ability to react with at least one target analyte. Located between the input segment and optic segment, the sensing slide is in fluid communication with the input segment and is in optical communication with the optic segment.

In another embodiment the current invention provides a replaceable sensing device. The replaceable sensing device comprises a lens and a mirror. The lens has a sensing surface that carries a plurality of reporters.

In another embodiment the current invention provides an apparatus for detecting a target analyte. The apparatus comprises a housing and a detector. The housing includes an input segment, a sensing slide and an optic segment.

The input segment is positioned within the housing and is adapted to receive and communicate a sample of analyte transport fluid carrying at least one target analyte to the sensing slide. The input segment includes a nozzle with a capillary. The capillary provides communication of the analyte transport fluid from outside the housing through the nozzle to a flow cell. The flow cell is in fluid communication with the capillary.

The sensing slide carries at least one reporter thereon, and is in fluid communication with the flow cell.

The optic segment is positioned within the housing, and is in optical communication with the sensing slide. The optic segment includes a light source adapted to generate a first wavelength, a lens, a mirror, and at least one optical excitation filter.

The first wavelength is adapted to generate a second wavelength when illuminating the reporter. The reporter is adapted to change the second wavelength when the reporter reacts with the target analyte. The lens is positioned adjacent to the sensing slide and has an index matching fluid separating it and the sensing slide. The lens is adapted to optically shift the second wavelength and the changed second wavelength to a new optical path. The optical emission filter is positioned to limit the spectral range of the second wavelength and the changed second wavelength.

The detector is in optical communication with the optic segment, and adapted to receive the second wavelength and the changed second wavelength.

An embodiment for a method of using the inventive apparatus comprises the following steps:

(a) a sampling of an analyte transport fluid with a collection device, the analyte transport fluid carrying at least one target analyte;

(b) illuminating a reporter positioned in the collection device with an illuminating source at a first wavelength, whereby during illumination the reporter fluoresces as a second wavelength, (c) detecting the second wavelength with a detector;

(d) reacting the target analyte with the reporter while continuing to illuminate the reporter at the first wavelength thereby producing a changed second wavelength; and (e) detecting the changed second wavelength.

In another embodiment, the present invention provides an optical detection device comprising a waveguiding capillary, an input segment, an optic segment and a detector.

The waveguiding capillary includes a first end and a second end. The capillary has a substrate applied on an inner wall. The substrate comprises a metallic layer applied to the inner wall, a dielectric layer applied to the first layer and at least one reporter layer applied to second layer. The first layer is preferably a metallic layer and the second layer is preferably a dielectric layer. The reporter is selected to react with at least one target analyte.

The input segment has a nozzle in fluid communication with first end of the capillary.

The optic segment is in optical communication with the waveguiding capillary. The optic segment includes a light source and an optical filter. The light source is adapted to provide optical excitement to the reporter. The light source is transversely positioned on a side of the waveguiding capillary. The light source generates a first wavelength. The illumination of the report with the first wavelength generates an emission at a second wavelength. The second wavelength undergoes a change during a reaction between the analyte and reporter. The optical filter is adapted to filter a portion of the second wavelength and the changed second wavelengths.

The detector is in optical communication with the optic segment. The detector is adapted to longitudinally receive the second wavelength and the changed second wavelength from the waveguiding capillary.

In yet another embodiment, the current invention provides an air sampling nozzle used with a SPCE sensor arrangement. The air sampling nozzle has a cylindrical receptacle with an open end and a receiving end. A borehole penetrates the receiving end to allow the sampled air to flow therethrough. The borehole is in fluid communication with a flow channel. The flow channel is formed by the receiving end and a SPCE sensing slide, wherein the area between the two forms the SPCE detection zone. The flow channel has a height of about 20 micrometers to about 100 micrometers. The flow channel is in fluid communication with an evacuation port to draw the sampled air therethrough. The air sampling nozzle is recessed within, and connected to, a mirror.

In still another embodiment, the current invention provides an air sampling nozzle. The air sampling nozzle comprises a cylinder having an open end and a receiving end. The receiving end of the cylinder has a first side facing the interior of the cylinder, and a second side facing opposite of the interior of the cylinder. At least one borehole penetrates the receiving end, and is in fluid communication with at least one flow channel. The flow channel is preferably disposed and positioned transversely in a recessed area of the receiving end second side. The flow channel is created by the receiving end second side, and a sensing surface on top of a SPCE slide, wherein the area between the two forms the SPCE detection zone. The flow channel preferably has a height of about 1 micrometer to about 1 centimeter with a preferred range of about 20 micrometers to about 100 micrometers. The flow channel carries the air sample across the sensing surface positioned on a reacting surface of the SPCE slide wherein the air sample interacts with the reactive coating. The flow channel preferably has an internal structure suitable for imparting a spiraling motion to the air sample flowing through the channel. The flow channel is in fluid communication with an evacuation port. The evacuation port provides a vacuum to draw fluid through the borehole and the flow channel. The cylinder is recessed within, and adjacent to, an inner focal point of an ellipsoidal mirror. The open end of the cylinder is preferably co-aligned with a foci end of the ellipsoidal mirror's external surface. The sensing surface is positioned at the first focal point of the ellipsoidal mirror.

Another embodiment of this invention is a fluorescence collection optical system. The fluorescence collection optical system has an ellipsoidal mirror. An emission source is optically positioned at the first foci of the ellipsoidal mirror. The emission source preferably comprises a surface plasmon coupled emission slide and fluorescence material coated on a reacting side of the surface plasmon coupled emission slide. The surface plasmon coupled emission slide is preferably a multilayered slide that is capable of redistributing the emission from the fluorescence material. The surface plasmon coupled emission slide has multiple metallic and dielectric thin layers coated on a transparent substrate. Preferably, the thickness and the refractive index of the dielectric layer specify the surface plasmon coupled emission angle. The surface plasmon coupled emission slide preferably has a reacting side and a mounting side. A reactive coating is positioned on the reacting side. The reactive coating on the reacting side of the surface plasmon coupled emission slide is comprised of fluorescence material such as CWIC or AFP. There is an emission source deposited on the reactive coating. Preferably, the emission source is a fluorescence material such as CWIC or AFP. The mounting side of the slide is attached to the flat side of a half-ball prism lens with index matching material. Preferably, the index matching material is an optical index matching fluid. The emission source has an analyte transport fluid flowing across and contacting the reacting side of the surface plasmon coupled emission slide. The emission source produces an excited emission light wave, such as the fluorescence, when stimulated. The excited emission light redistributed by the surface plasmon couple emission mechanism is hence allowed to penetrate through the substrate of the surface plasmon coupled emission slide and the index matched half-ball prism lens. The presence of the prism lens allows the excited emission light to exit the prism lens without being trapped by the total internal reflection.

In the fluorescence collection optical system, the excitation assembly contains an excitation filter and a light source. The excitation assembly is affixed to the back of the half-ball prism lens. The excitation filter is positioned between the light source and the half-ball prism lens. The light source provides the stimulus to excite the emission source through the excitation filter and is loosely focused by the half-ball prism lens. A spatial filter is inserted in the optical path to filter any light wave traveling within the ellipsoidal mirror. The spatial filter limits the angle of the reflected emission of the excited light wave, and blocks the undesired light such as the scattered excitation and ambient light. The spatial filter is configured to allow the excited emission light wave to pass through with specified transmission angles ranging from 55 degrees to about 85 degrees. The excitation assembly affixed to the back of the half-ball prism lens blocks any light wave with a transmission angle of less than 55 degrees. An emission detection sensor is positioned at the second foci of the ellipsoidal mirror. The emission detection sensor is preferably a photodetector used in conjunction with an optical filter having a band-pass matched to the emitter. The photodetector is capable of receiving the spatially filtered excited emission light wave through another emission filter. The emission filter provides additional spectral filtering, and increases the signal-to-noise ratio of the collection emission signal.

In still another embodiment of this invention is a miniaturized optical emission collection system. The miniaturized optical collection system is contained in a cylindrical housing. The miniaturized optical emission collection system comprises a reverse half-ball prism lens having a flattened vertex on the convex of the reverse half-ball prism lens. The flattened vertex provides optical contact and is index matched to the substrate side of the surface plasmon coupled emission slide. The surface plasmon coupled emission slide has multiple metallic and dielectric thin layers coated on a transparent substrate. Preferably, the thickness and the refractive index of the dielectric layer specify the surface plasmon coupled emission angle. The surface plasmon coupled emission slide has a reacting side and a mounting side. A reactive coating is positioned on the reacting side. The reactive coating on the reacting side of the surface plasmon coupled emission slide is an optical reporter or emission source. Preferably, the emission source is a fluorescence material such as CWIC or APP. The mounting side of the slide is attached to the flattened vertex with index matching material. Preferably, the index matching material is an optical index matching fluid. The emission source has an analyte transport fluid flowing across and contacting the reacting side of the surface plasmon coupled emission slide.

The miniaturized optical emission collection system further comprises a miniaturized air sampling nozzle on the first end of the cylindrical housing. The miniaturized air sampling nozzle is comprises a thin disk having a first side exposed to the ambient air, and a second side facing the reacting side of the surface plasmon couple emission slide. The miniaturized air sampling nozzle is in fluid communication with a flow channel. The flow channel is formed by the void created between the thin disk and the surface plasmon coupled emission slide. The flow channel is about 20 micrometers to about 100 micrometers in height. The thin disk has a borehole proximate to the center of the thin disk. The thin disk also has an exhaust port proximately to an outer edge. A pump affixed to the exhaust port provides a sufficient pressure drop to create vacuum at the borehole. An air sample containing an analyte is pulled into the flow channel through the borehole. The air sample flows through the flow channel and across a sensing space. The sensing space is proximate to the reacting side of the surface plasmon coupled emission slide, and the flow channel. The flow of the air sample through the flow channel permits the air sample containing the analyte to flow across and react with the reacting side of the surface plasmon coupled emission slide. Preferably, the flow channel is a spiraling flow channel causing the air sample to have a spiraling motion as it flows across the reacting side of the surface plasmon coupled emission slide.

The miniaturized optical emission collection system has an excitation filter. The excitation filter has a first side affixed to the center of a substantially flat surface of a half-ball prism lens. The excitation filter is positioned between the light source and the half-ball prism lens, where the light source provides a stimulus to excite the emission source. The emission source such as the fluorescence material on the sensing surface produces an excited emission light wave when stimulated. The emission light wave penetrates through the surface plasmon coupled emission slide substrate and enters the vertex of the half-ball prism lens with a transmission angle greater than the critical angle. The incidence of the emission light onto the concaved internal surface of the half-ball prism lens results in total internal reflection, which causes the emission light to bounce around the internal surface until it reaches the substantially flat surface of the prism lens. The excited emission light is filtered through a spatial and a spectral filter. A spatial filter is affixed to a substantially flat surface of the half-ball prism lens, and has at least one notch for filtering the desired emission light wave. A spectral filter is positioned to filter the excited light prior to hitting the photodetector. A photodetector sensor that is capable of receiving the filtered emission light wave is used. The entire system is encased within an excitation assembly. The half-ball prism lens is about 10.0 millimeters or less in diameter. The spatial filter is configured to allow the emission light wave to pass through with a transmission angle of about 70 degrees to about 80 degrees.

Another embodiment of this invention is a compact optical emission collection device. The compact optical emission collection device comprises a reverse half-ball prism lens having a flattened vertex, a surface plasmon coupled emission slide, and an air sampling nozzle. The reverse half-ball prism lens flattened vertex is positioned on the convex of the reverse half-ball prism lens. The flattened vertex provides optical contact, and is index matched to the substrate side of surface plasmon coupled emission slide. The surface plasmon coupled emission slide has multiple metallic and dielectric thin layers coated on a transparent substrate. Preferably, the thickness and the refractive index of the dielectric layer specifies the surface plasmon coupled emission angle. The surface plasmon coupled emission slide has a reacting side and a mounting side. A reactive coating is positioned on the reacting side. The reactive coating on the reacting side of the surface plasmon coupled emission slide is comprised of an optical reporter or emission source. Preferably, the emission source is a fluorescence material such as CWIC or AFP. The mounting side of the slide is attached to the flattened vertex with index matching material. Preferably, the index matching material is an optical index matching fluid. The emission source has an analyte transport fluid flowing across and contacting the reacting side of the surface plasmon coupled emission slide.

The compact optical emission collection system further comprises a miniaturized air sampling nozzle on the first end of the cylindrical housing. The miniaturized air sampling nozzle is comprised of a thin disk having a first side exposed to the ambient air, and a second side facing the reacting side of the surface plasmon couple emission slide. The miniaturized air sampling nozzle is in fluid communication with a flow channel. The flow channel is formed by the void created between the thin disk and the surface plasmon coupled emission slide. The flow channel is about 20 micrometers to about 100 micrometers in height. The thin disk has a borehole proximate to the center of the thin disk. The thin disk also has an exhaust port proximate to an outer edge. A pump affixed to the exhaust port provides a sufficient pressure drop to create vacuum at the borehole. An air sample containing an analyte is pulled into the flow channel through the borehole. The air sample flows through the flow channel and across a sensing space. The sensing space is proximate to the reacting side of the surface plasmon coupled emission slide, and the flow channel. The flow of the air sample through the flow channel permits the air sample containing the analyte to flow across and react with the reacting side of the surface plasmon coupled emission slide. Preferably, the flow channel is a spiraling flow channel causing the air sample to have a spiraling motion as it flows across the reacting side of the surface plasmon coupled emission slide.

Preferably, the compact optical emission collection device propagates the emission light along the concaved internal surface inside the reverse half-ball prism lens providing an emission light path which is proximate to the air/prism lens interface. The excitation light source assembly, which includes a light source and an excitation filter, is preferably embedded in the prism lens proximate to a flattened vertex. The excitation light source is preferably positioned such that the emission light path is not obstructed by the assembly. The embedded excitation assembly allows the light receiving assembly, which includes the spatial filter, spectral filter, and the photodetector, to be proximately positioned to the substantially flat surface of the prism lens. A molded optics fabrication process may be used to encapsulate the light source and the excitation filter into a half spherical dome to realize a very compact excitation and collection optical stack.

BRIEF DESCRIPTION OF THE DRAWINGS

FIG. 4 is a detail view of the sensing slide with a plurality of reporters thereon.

FIG. 13 depicts the test results for the reaction time from a reaction versus the intensity for a given temperature of the analyte.

FIG. 14 depicts the fluorescence test results of the resulting wavelength from a reaction versus the angle of the emission for given temperature of the analyte showing the angular and spectral distribution of the AFP emission.

FIG. 15 depicts the spectrum of the fluorescence test results taken at an angle of about 64 degrees.

FIG. 16 depicts a test result for Dinitrotoluene (DNT) at the 465 nanometer, 495 nanometer and 515 nanometer wavelengths using the inventive embodiments.

FIG. 17 depicts a test result for Nitroglycerin (NG) at the 465 nanometer, 495 nanometer and 515 nanometer wavelengths using the inventive embodiments.

DETAILED DESCRIPTION

Figure 1A:
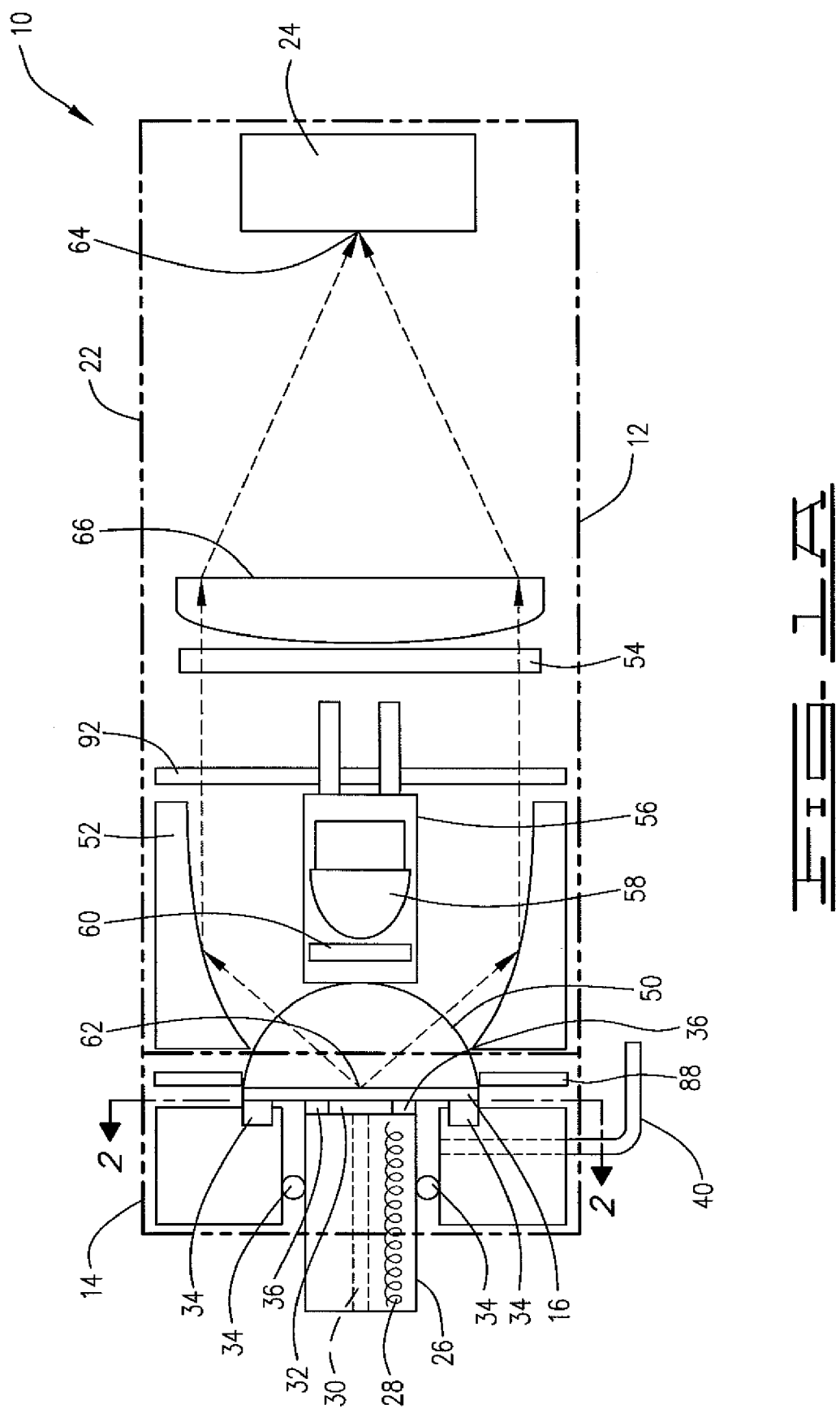
FIG. 1A schematically depicts a first embodiment of a SPCE sensor.

This invention provides for an apparatus to optically collect and detect changes in a fluorescing emission resulting from the reaction of an explosive, chemical or biological warfare substance with a reporter material such as a chemical warfare indicating chromophore (CWIC) or amplifying fluorescence polymer (AFP) material. The apparatus comprises three main elements: an air sampling nozzle, fluorescence collection optics, and a detector/sensor.

I. SPCE Overview

Surface plasmon resonator (SPR) sensors are frequently used as surface binding detection techniques in chemical and biological material sensing applications. Due to the presence of a SPR-capable metal surface, an emission from a CWIC or AFP is coupled into the surface plasmon wave (SPW) and then re-radiated as SPCE via the surface plasmon coupled emission phenomenon. The SPW is a surface-bonded electromagnetic wave propagation in which the free electrons in a conductor, such as coated thin films of noble metals, collectively oscillate in an excited state resulting from stimulation from an excitation light. The SPW excitation condition, such as the incident angle of an excitation light, is highly sensitive to changes in the surface conditions. The interaction of the analyte with the sensing surface is detected by tracking the change in the SPW excitation condition (e.g., SPR angle).

The commonly employed SPR sensor arrangement is the Kretschmann setup. In the Kretschmann setup, p-polarized transverse magnetic mode interrogation light, or excitation light, with wave vector $k_o$ is incident through a high refractive index prism on the thin metal film. The SPW is excited by the incident light when the following phase matching condition is met:

$$n_p k_o \sin\theta = k_{spw}, \text{ and } k_o = 2\pi/\lambda_o,$$

where $k_{spw}$, $n_p$, and $\theta$ are the SPW wave vector, refractive index of prism, and incident angle, respectively. When the excitation light with a wavenumber ($k_o$) is incident with the SPR angle ($\theta_{spr}$), the SPR occurs and reflection is minimized. The SPR angle is very sensitive to the change of the thickness or refractive index deposited on the analyte-side of the metal film.

The present invention uses SPCE as a means to extract the fluorescing emission into a high signal-to-noise zone. SPCE is characterized as the opposite process of the above mentioned SPR energy conversion process. The SPCE-capable surface typically has a transparent substrate (e.g. glass or quartz substrate), and a thin metallic coating on top of the substrate. Preferably, a thin layer of dielectric coating is deposited on top of the metallic layer, which provides a separation between the emitter and metallic surface. Additionally, the dielectric coating provides protection to the thin metallic layer. Instead of converting the incident plane wave energy to the SPW, the spontaneous emission from the spontaneous emitter on the SPCE-capable surface at the proximity of the metal surface is first coupled into the SPW, and then converted into far-field radiation that propagates through the substrate where it is subject to detection.

The SPCE coupling condition is essentially governed by the same SPR phase matching condition at the emission wavelength identified in the equation above. To determine the fluorescence distribution of SPCE, the wave vector $k_o$ is replaced by $k_{spce}$ and $\theta_{spr}$ by $\theta_{spce}$. Due to emission constraints imposed by the phase matching condition, the p-polarized radiation source, or emitter, has a specified spatial emission distribution instead of the more common isotropic emission in the homogeneous media. The specified spatial emission distribution is an emission cone with peak intensity centered at the "SPCE angle", $\theta_{spce}$. The SPCE angle is the transmission angle between the SPCE beam, and the substrate surface normal (toward the substrate).

SPCE has the characteristic of a highly confined emission distribution for p-polarized radiation. Such a focused, highly confined emission distribution allows the fluorescence emission pattern to be collected more efficiently with excellent spatial and polarization filtering options for better discrimination. Usually, free-space spontaneous emission collection efficiency is about 1% due to the isotropic emission pattern. A SPCE-type of system has a spontaneous emission collection efficiency up to 50% to about 60% within the focused SPCE emission cone.

The fluorescence distribution pattern in SPCE is essential for optimizing detection of the explosive, chemical or biological substances reacting with the CWIC or AFP material. The angular SPR reflection curves of the SPCE slides can be used to estimate the fluorescence distribution from the SPCE slide. This has been proven in the literature, and through experimentation.

Figure 8:
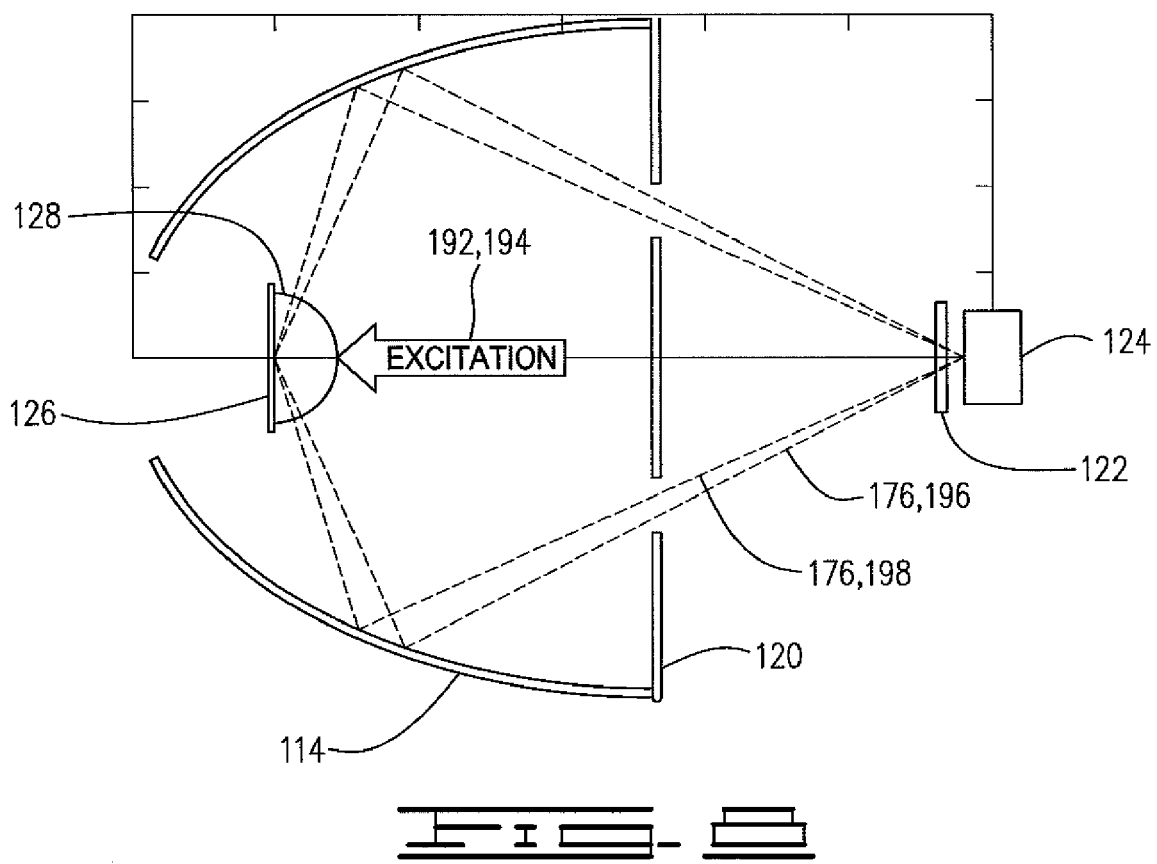
FIG. 8 schematically depicts the ray tracing for the first embodiment of a SPCE sensor arrangement using an ellipsoidal mirror.

By way of a non-limiting example, to collect wide-angle emissions, an ellipsoidal mirror or half-ball prism lens is used instead of high numerical aperture optics. By positioning the fluorescent emission at one of the foci of the ellipsoidal mirror, the SPCE signal is focused at the other focal point upon the photo detector sensors. Because of this arrangement, there exists a well-defined SPCE emission angle which allows a spatial filter mask to be designed by using a ray tracing method as shown in FIG. 8. The ray tracing depicted in FIG. 8 shows the two-dimensional presentation of the example setup and ray tracing results. The spatial filter removes a substantial portion of the unwanted excited light and background noise from the emissions. The light source, or excitation light, illuminates the SPCE slide through the half-ball prism lens. The photodetector is positioned at the other focus to collect the SPCE fluorescing emission through the spatial filter mask. To increase the SNR of the captured emissions, an optional emission filter is used in front of the photodetector to further reduce unwanted light reaching the photo detection sensor.

The SPCE angle for the emission is much greater than the critical angle. The larger emission angle opens up the possibility of using the forbidden light principle to detect an explosive, chemical or biological substance with by using a high SNR technique. One reason for using SPCE is the ability to reject free-space ambient light. The ambient light is only allowed to go into the "allowed light" zone, where the transmission angle is smaller than the critical angle. Essentially, the "allowed light" transmitted is rejected by the "forbidden light" zone. Only through a near-field coupling effect, such as SPCE, can the light propagate into the "forbidden light" zone. This technique has a transmission angle greater than the critical angle. Therefore, SPCE can be detected in the "forbidden light" zone, which has very low background light. This enables sensitive fluorescence detection due to the high SNR of the signal.

II.A Apparatus Background Information

The various reporters suitable for detecting explosives have different types of fluorescent responses when reacted with an analyte. For example, a reporter may initially be non-responsive when excited by a light source, but after reacting with the analyte will fluoresce at a detectable wavelength when excited by that light source. Another reporter may fluoresce when excited by a light source and subsequently experience an increase in fluorescent emission intensity after reacting with the analyte. Such reporters are sometimes referred to as "turn-on" reporters. Another type of reporter may initially emit fluorescent light when excited by a light source, but after reacting with the analyte will then emit less intense or no fluorescent light during the continued excitement from the light source. This type of response to the analyte reaction is called "quenching". The spectrum of the fluorescent light may change after reacting with the analyte, increasing the emission at some wavelengths and/or decreasing the emission at other wavelengths. These changes may be reversible or irreversible depending upon the reporter and/or analyte.

By way of a non-limiting example the following reporters provide some of the responses identified above and herein: (a) CWIC group of reporters are a "turn-on" type of reporter and (b) AFP is a quenching type of reporter. Other types of reporters known to those skilled in the art will also provide responses as identified herein.

The terms "react" and "reacting" used herein indicates actions the reporter takes in response to the presence of an analyte. In the instance of fluorescence, the reporter may change the intensity of fluorescence or emit a different wavelength.

II.B Apparatus

The first preferred embodiment is depicted in FIGS. 1A-5 as an apparatus for an optical collection and detection device 10. Device 10 comprises housing 12 having an input segment 14, sensing slide 16 and optic segment 22 positioned within housing 12. Device 10 provides optical input to detector 24. Preferably, detector 24 is also positioned within housing 12.

Input segment 14 includes air sampling nozzle 26, heating source 28, capillary 30, and flow cell 32. Input segment 14 samples the air and communicates an analyte transport fluid to sensing slide 16. Analyte transport fluid carries at least one analyte which is communicated to sensing slide 16. Analyte transport fluid is commonly an air sample of interest obtained in an area of interest, such as at an airport screening location, a shipping container receiving point, or other locations where analytes might appear.

As shown in FIGS. 1A and 4, air sampling nozzle 26 is secured and stabilized within housing 12 by o-ring spacer 34. Spacer 34 is preferably an o-ring that does not outgas or absorb chemical substances. Furthermore, spacer 34 should not react with chemical substances.

Air sampling nozzle 26 is separated from sensing slide 16 by c-ring 36. C-ring 36 is preferably a material that minimally absorbs analytes. One example of c-ring 36 is using a non-stick material such as Teflon®. C-ring 36 provides a standoff spacing between the end facet of capillary 30 and sensing slide 16. C-ring 36 preferably has a thickness of about 50 to about 75 micrometers. The thickness of c-ring 36 defines the height of flow cell 32. Additionally, c-ring 36 has ring slot 38 providing fluid communication of the analyte transport fluid with sensing slide 16 from capillary 30.

Capillary 30 is disposed within air sampling nozzle 26. Preferably, capillary 30 is silanized to reduce any analyte consumption during passage of the analyte transport fluid. Capillary 30 receives the analyte transport fluid and communicates it to flow cell 32. Flow cell 32 is in fluid communication with sensing slide 16 and with fluid exit 40. Fluid exit 40 is the exhaust port for air sampling nozzle 26. The flow of analyte transport fluid through air sampling nozzle 26 may be assisted by a pump (not shown) attached to fluid exit 40. The preferred flow rate of the analyte transport fluid is about 30 milliliters per minute. The analyte transport fluid is temperature and flow stabilized while being communicated through capillary 30.

Preferably, analyte transport fluid is heated by a sampling unit (not shown) prior to being sampled by air sampling nozzle 26. When employed, the sampling unit becomes a first stage or portion of the input segment. Capillary 30 serves as a flow stabilizer and provides thermal buffering between the heated input from the sampling unit and sensing slide 16. This approach encourages the analyte adsorption and desorption on sensing surface 18.

An alternative embodiment employs heating source 28 to heat analyte transport fluid while it is being communicated through capillary 30. When using the alternative embodiment, heating source 28 is embedded within air sampling nozzle 26 and is adapted to heat air sampling nozzle 26 to a desired temperature. In this alternative embodiment, heating source 28 heats the analyte transport fluid sufficiently so as to provide the analyte transport fluid at sensing slide 16 at a temperature of about 40 degrees Celsius. Preferably, the analyte transport fluid is heated between about 40 degrees Celsius and about 120 degrees Celsius.

As seen in FIGS. 1A-4, sensing slide 16 is positioned between input segment 14 and optic segment 22. In this embodiment, sensing slide 16 is circularly shaped and has sensing surface 18 oriented towards the flow of the analyte transport fluid. Sensing slide 16 has non-sensing surface 20 oriented away from the flow of the analyte transport fluid.

Figure 2:
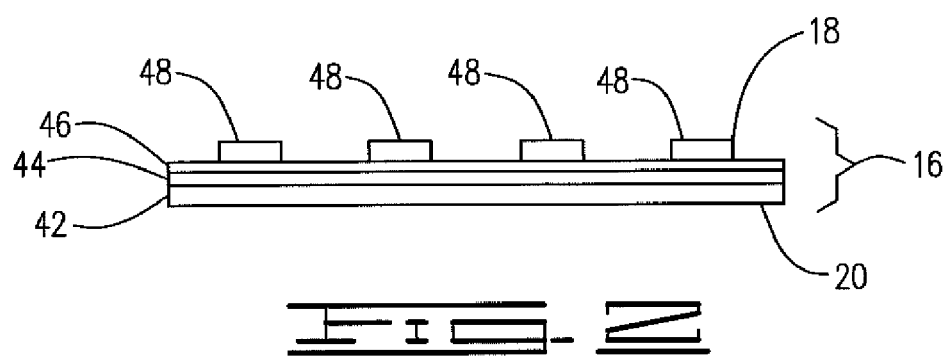
FIG. 2 is a schematic view of the sensing slide taken along line 2-2 of FIG. 1A.
Figure 3:
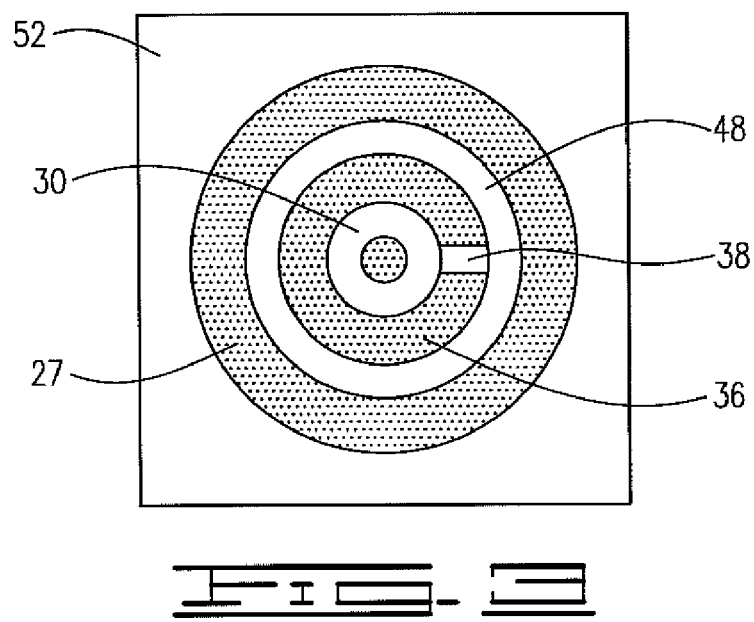
FIG. 3 is a schematic end-view of the capillary and flow cell.

Sensing slide 16, shown in FIG. 2, is preferably a glass substrate 42 coated with a plurality of substrate layers on sensing surface 18. First layer 44 is preferably a metallic layer of a film made of a metal or a metal alloy. Examples of metals include silver, gold, platinum, or aluminum. First layer 44 is applied directly to glass substrate 42. Second layer 46 is applied to first layer 44. Second layer 46 is preferably a dielectric overcoat layer. Reporter 48 is applied to the second layer, thereby forming a third layer. Preferably, reporter 48 is a CWIC or AFP and is adapted to react with the analyte carried by the analyte transport fluid.

Figure 5:
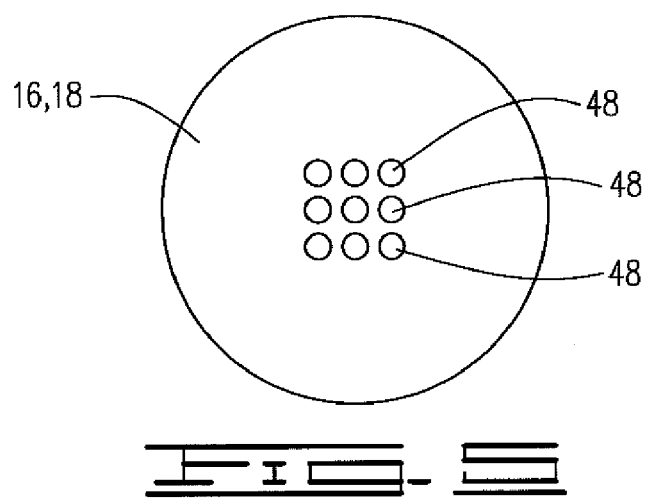
FIG. 5 schematically depicts the optical layout for the inventive embodiments.
Figure 5:
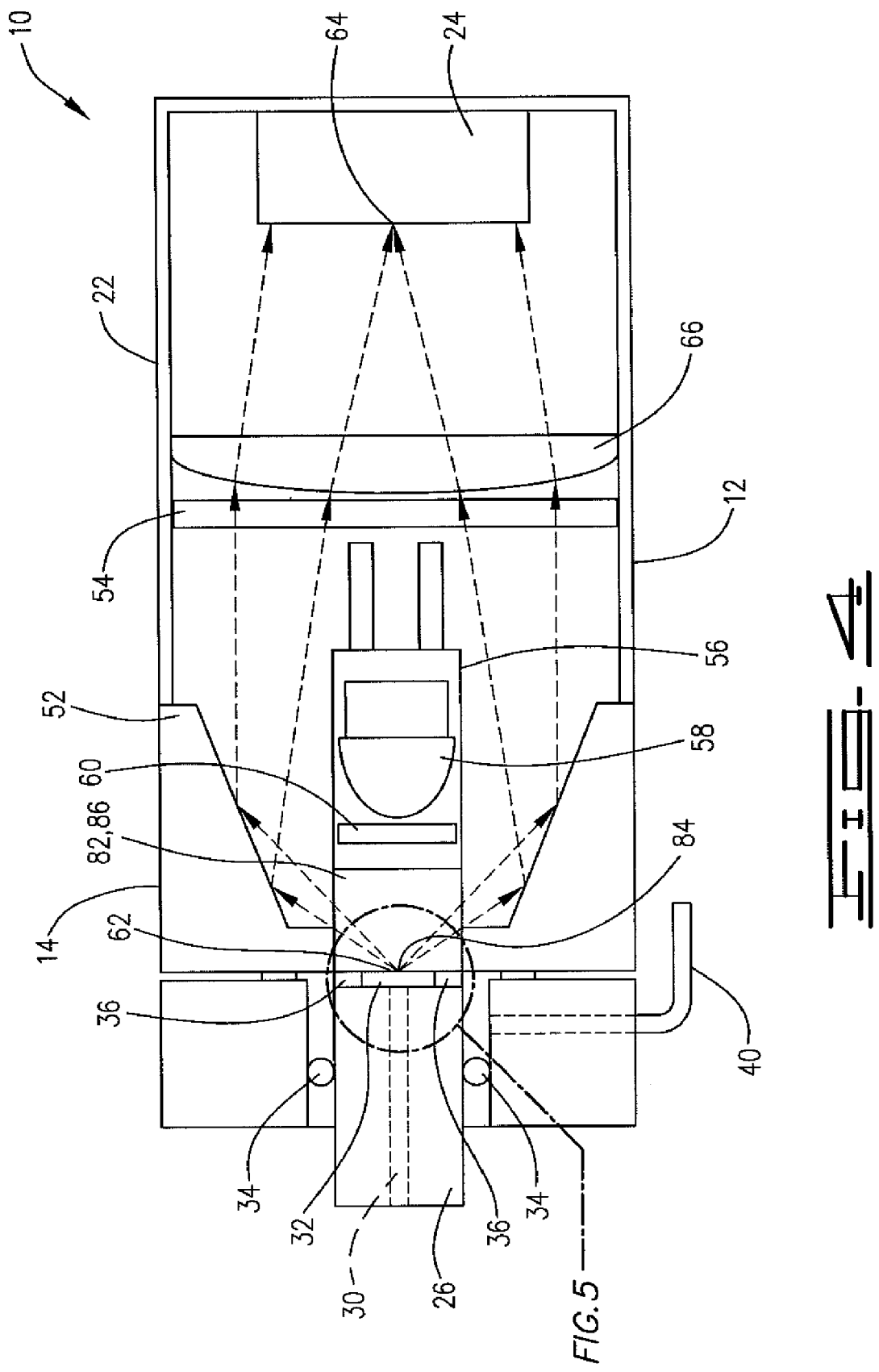

Preferably, reporter 48 is applied to second layer 46 to form a deposition spot size of about several hundred micrometers in diameter. Reporter 48 may be applied in an array of a plurality of reporters 48 as shown in FIG. 5. When applied in an array of a plurality of reporters 48, each reporter 48 reacts to a different analyte carried in the analyte transport fluid when there is a plurality of analytes present. Preferably, the array of a plurality of reporters 48 is positioned on sensing slide 16. The array is preferably a single array having a total area of about 10 millimeters squared to about 1 millimeter squared or smaller.

Figure 1:
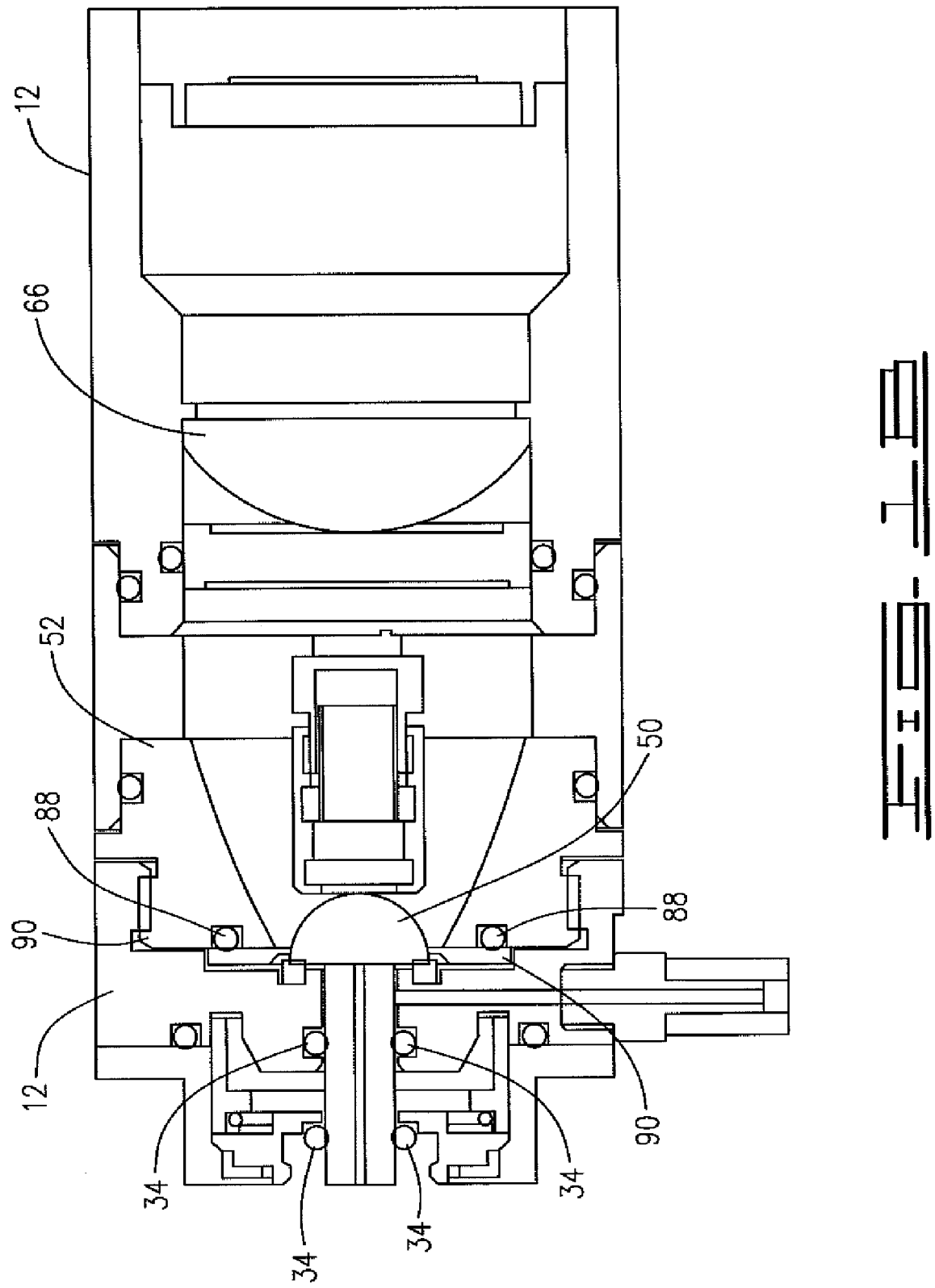
FIG. 1B is a section view of the device from the first embodiment and schematically depicted in FIG. 1.

As shown in FIGS. 1A and 4, optic segment includes lens 50, mirror 52, excitation assembly 56 and optical emission filter 54. Excitation assembly 56 further includes light source 58 and optical excitation filter 60. Optical segment 22 is in optical communication with sensing slide 16. Optical segment 22 is also in optical communication with detector 24. As shown in FIGS. 1 and 4, the optical path flows from light source 58 through excitation filter 60 to reporter 48. The emission from reporter 48 flows through lens 50 to mirror 52 and through emission filter 54 before reaching detector 24.

Lens 50 is attached to sensing slide 16 by an index matching fluid. The index matching fluid eliminates air between lens 50 and sensing slide 16. Lens 50 is shown in FIGS. 1 and 4. Preferably, lens 50 is a half-ball lens as described herein. When assembled, lens 50 is pressed against sensing slide 16 and c-ring 36 by a lens holder (not shown) formed in housing 12 and held in place by lens mount 88, as shown in FIG. 1A.

Mirror 52 may be an ellipsoidal, conical or parabolic mirror. When mirror 52 is shaped as an ellipsoid or a parabola, reporter 48 on sensing slide 16 is optically positioned at first foci 62 of mirror 52. When mirror 52 is shaped as a conical mirror, sensing slide 16 is positioned relative to the cone reflector so that any resulting emission (wavelength) is directed toward the receiving area 64 of detector 24. Mirror 52 is aligned with respect to lens 50. Lens 50 is immobilized by lens mount 88 and mirror mounting structure 90, as shown in FIG. 1B.

Referring to FIG. 1B, structural member 92 is shown supporting excitation assembly 56. However, any mounting assembly capable of holding excitation assembly in housing 12 and not block light transmission may be used in this invention.

Excitation assembly 56 is positioned to illuminate reporter 48 with a light wave having a first wavelength from light source 58. As referred to herein, "wavelength" is understood to refer to both the light wave and the associated wavelength of that light wave. Preferably, light source 58 is a light emitting diode (LED) emitting a light. First wavelength from light source 58 may produce a plurality of wavelengths based upon the type of light source 58 employed. Light source 58 may be any light source 58 that produces a light having a wavelength band capable of producing a response in reporter 48. A non-limiting example of acceptable light sources 58 includes LEDs and lasers. The first wavelength emitting from light source 58 is filtered by excitation filter 60 prior to the first wavelength reaching reporter 48. Excitation filter 60 may be a short band pass filter or a band pass filter. The plurality of wavelengths are also filtered by first optical filter 60 to allow the desired wavelengths to reach reporter 48.

The first wavelength generates fluorescing by reporter 48. The fluorescing reporter 48 emits a second wavelength that, is different from the first wavelength emitted from light source 58. When reporter 48 reacts with the analyte, the fluorescing changes and a third, or changed, wavelength is emitted therefrom, Both the second and third wavelengths are refracted through sensing slide 16 to mirror 52. In practice there may be multiple wavelengths emitted by reporter 48 in response to the first wavelength and when reacting with the analyte.

Mirror 52 reflects the second and third wavelengths towards detector 24. Preferably, prior to the second and third wavelengths reaching detector 24, they are filtered by second optical filter 54. Additionally, an optional focusing lens 66 may be utilized to shorten the optical path length of optical segment 22 by focusing the second and third wavelengths on receiving area 64 of detector 24.

An alternative embodiment is shown in FIG. 4. For this alternative, sensing slide 16 and lens 50 are replaced with sensing segment 82. Sensing segment 82 has facet surface 84 upon which first layer 44, second layer 46, and reporter 48 are applied. Preferably, first layer 44 is a metallic layer and second layer 46 is a dielectric layer. Reporter 48 is the third layer and is applied to second dielectric layer 46. Sensing segment 82 is preferably a transparent dielectric cylinder. Some non-limiting examples of materials for dielectric cylinder are glass, fused silica, or quartz. In this alternative embodiment, mirror 52 is a conical mirror 52. Sensing segment 82 serves as a cylindrical lens and the emission exits from its side surface 86.

Sensing segment 82 preferably carries at least one reporter 48. If a plurality of reporters 48 are used, reporters 48 are distributed within 3 millimeters from the center of facet surface 84. The shifted reporters 48 provide a shift in reflection of the reacting analyte and reporter 48.

Sensing segment 82 is adapted to be easily removed from the device in a field environment and replaced in the same environment. The field is anywhere the device is employed. For example, sensing segment 82 is adapted to fit within a cartridge (not shown) that locks into housing 12. Alternatively, sensing segment is directly inserted and removed from housing 12 without requiring cartridge. Upon depletion of reporter 48, the cartridge or sensing segment 82 is removed from housing 12 and a new cartridge or sensing segment 82 is inserted into housing 12.

Figure 6:
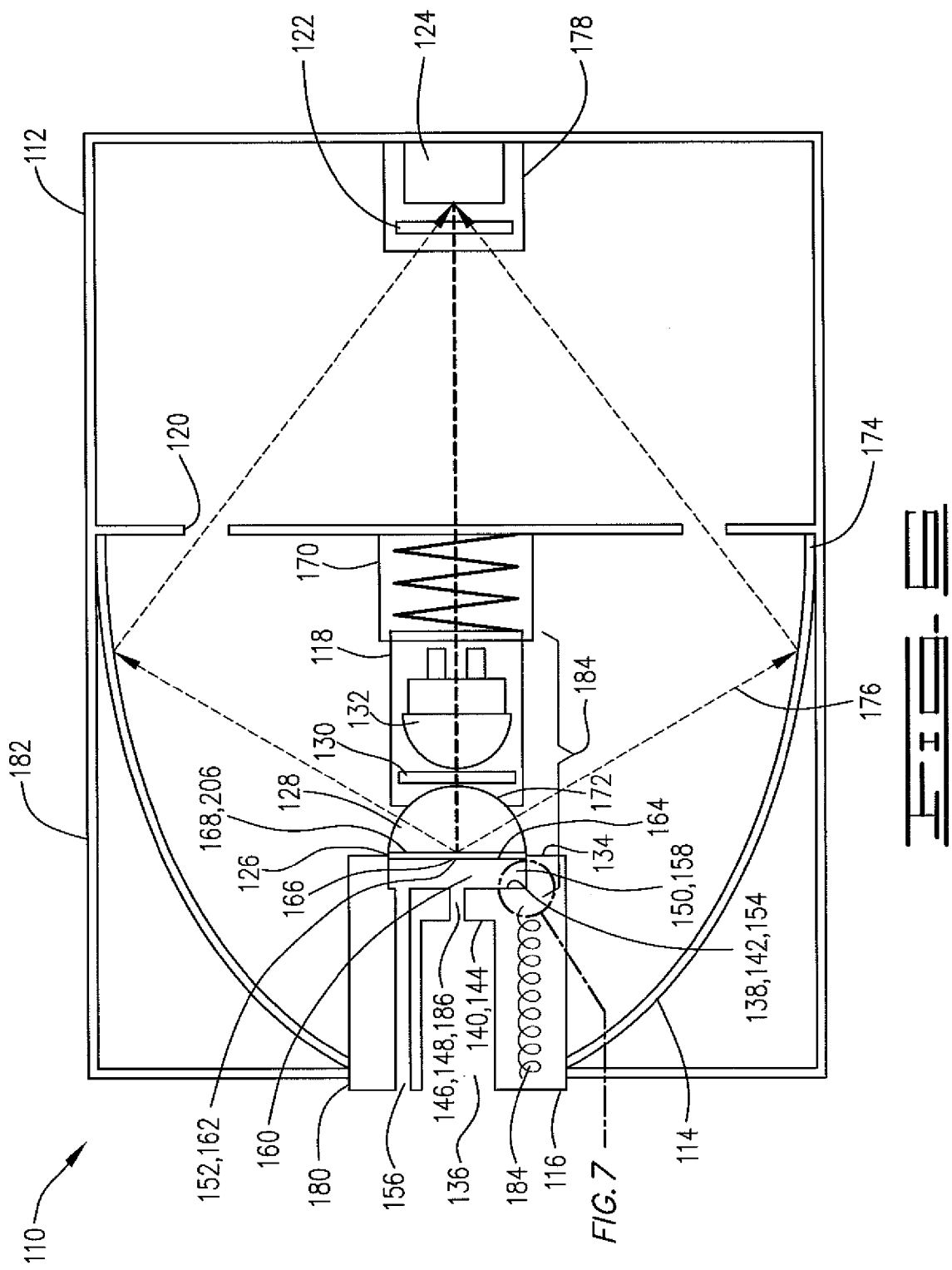
FIG. 6 schematically depicts a first embodiment of a SPCE sensor arrangement using an ellipsoidal mirror.
Figure 7:
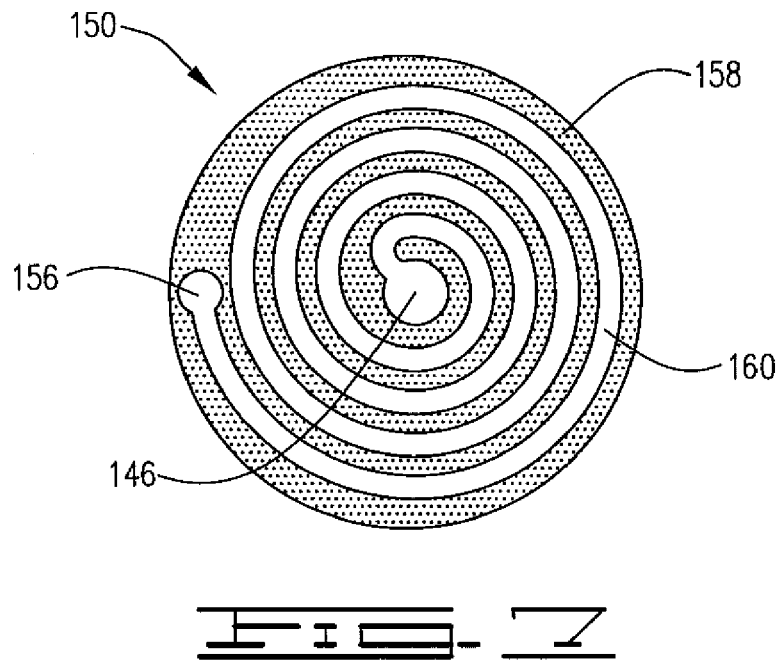
FIG. 7 schematically depicts a spiraling flow channel used in the first, second and third embodiments.

Referring to FIGS. 6-8, in another embodiment, optical collection and detection device 110 includes housing 112 having an input segment 180, sensing slide 126 and optic segment 182 positioned therein. Input segment 180 includes air sampling nozzle 116, heating source 184, borehole 146, and flow cell or channel 150. Input segment 180 is in fluid communication with sensing slide 126. Optical segment 182 includes mirror 114, excitation assembly 118, spatial optical filter 120 and emission optical spectral filter 122. Optical segment 182 is in optical communication with sensing slide 126, Photodetector 124 is in optical communication with optical segment 182.

Sensing slide 126 and half-ball prism lens 128 are held in place by air sampling nozzle 116 and excitation assembly 118. Excitation assembly 118 includes an excitation filter 130 and a light source 132, which is preferably a light emitting diode (LED). However, light source 132 may be any light source cable of generating fluorescence in the reaction of an analyte with CWICs or AFPs, collectively referred to as reporters 48. For example, light source 132 may include LEDs and solid-state lasers.

Using air sampling nozzle 116, input segment 180 samples an air mixture and provides device 110 with the analyte transport fluid containing an analyte. Air sampling nozzle 116 communicates the analyte transport fluid through borehole 146. There may be a plurality of analytes in the analyte transport fluid. FIG. 6 depicts air sample nozzle 116 positioned within housing 112 and part of ellipsoidal mirror 114.

In this embodiment, air sampling nozzle 116 includes cylinder 134, cavity 136, open end 138, receiving end 140, first borehole 146, flow channel 150 and exhaust port, or evacuation port 156. Receiving end 140 of cylinder 134 has first side 144 facing receiving end 140 and second side 142 oppositely positioned. Cylinder 134 has first borehole 146 penetrating center 148 of receiving end 140, and providing fluid communication between cavity 136 and flow channel 150.

Flow channel 150 is formed by open end 138 of air sampling nozzle 116, and the sensing surface 152 of sensing slide 126. Flow channel 150 is preferably disposed and positioned in recessed area 154 of second side 142. Flow channel 150 preferably has a height of about 20 micrometers to about 100 micrometers. Flow channel 150 preferably has an internal structure 158 suitable for imparting a spiraling motion to fluid flowing through flow channel 150 such that the fluid flows through sensing space 160, and across sensing slide 126 with an extended, or elongated, interaction path length between the air sample and sensing slide 126. Internal structure 158, which is used to form the flow channel 150, may be machined onto the surface of second side 142.

In operation, cavity 136 is an initial air sample collection zone. Borehole 146 provides fluid communication between sensing space 160, as defined herein, and cavity 136. Evacuation port 156 provides fluid communication between sensing space 160 and the atmosphere or a suitable small pump (not shown). Evacuation port 156 provides a conduit for a vacuum to draw fluid through first borehole 146 and flow channel 150. In the embodiment depicted in FIG. 6, the small pump creates a vacuum, and draws the sampled air through first borehole 146 and across sensing slide 126.

SPCE detection zone, or sensing space 160, is located in flow channel 150 between second side 142 and sensing surface 152 of sensing slide 126. Sensing surface 152 is the location where an analyte reacts with reporter 48. Upon sensing surface 152, reporter 48 is illuminated with first light wave 192 propagating first wavelength 194 from light source 132. First wavelength 194 causes reporter 48 to fluoresce. Reporter 48 emits a fluorescing, or second, wavelength 196. The reacting analyte and reporter 48 create a change in second wavelength 196 and emit a changed, or third, wavelength 198.

Sensing slide 126 is also referred to as a "SPCE slide," and is preferably a glass or quartz substrate coated with a plurality of layers of substrate. In the preferred embodiment, sensing slide 126 is similar to sensing slide 16 depicted in FIG. 2. Sensing slide 126 carries first layer 44 and second layer 46. Preferably, first layer 44 is a metallic layer and second layer 46 is a dielectric layer. Reporter 48 is a third layer applied on top of second layer 46. Sensing slide 126 is preferably adapted to provide a SPCE angle between about 55 to about 85 degrees.

First layer 44 is about 20 nanometers to about 70 nanometers. If silver is employed, it is preferably about 50 nanometers. However, first layer 44 may be other SPR-capable metals such as aluminum, gold, or platinum. The choice depends upon the desired fluorescence wavelengths.

Second layer 46 in one specific implementation is silicon dioxide ($SiO_2$) with a thickness of about 5 nanometers to about 30 nanometers. Poly-vinyl alcohol (PVA) has also been successfully tested as the dielectric layer. The SPCE emission angle is dictated by the dielectric thickness. Thus, the thickness of second layer 46 is dependent on the desired application.

Sensing slide 126 has a reacting side 162 and a mounting side 164. Reacting side 162 is sensitized with reporter 48 and fluoresces when illuminated. Sensing space 160 is positionally located immediately above sensing slide 126 on reacting side 162. Reacting side 162 is also positioned to be at first focal point 166 of ellipsoidal mirror 114. Mounting side 164 is affixed to flat portion 168 of a half-ball prism lens 128 with an optical index matching fluid 206. Optical index matching fluid 206 is required to remove any unintended air gap between half-ball prism lens 128 and sensing slide 126. Half-ball prism lens 128 is extended into area 154, and is retained by excitation assembly 118. Half-ball prism lens 128 may also be another shape of a prism having a cylindrical symmetry.

Spring loaded cylinder 170 exerts a force that presses excitation assembly 118 against half-ball prism lens 128 curved side 172. Spring loaded cylinder 170 also exerts a force that presses against spatial filter 120. As indicated, excitation assembly 118 also carries excitation filter 130 and light source 132. Excitation filter 130 is positioned between half-ball prism lens 128 and light source 132 to block light of undesired wavelength. Excitation assembly 118 also functions as a part of spatial filter 120 and blocks emissions from the sensing surface 152 of sensing slide 126 which transmits through half-ball prism lens 128 with a transmission angle smaller than 55 degrees.

Optional spatial filter 120 is transversely affixed across open end 174 of ellipsoidal mirror 114, as shown in FIGS. 6 and 8. Spatial filter 120 blocks transmitted light emissions 176, and removes a substantial portion of the unwanted fluorescing emission and background noise. Spatial filter 120 is adapted to provide transmission angles within a tunable range. The tunable range is typically between about 55 degrees to about 85 degrees. Ellipsoidal mirror 114 focuses transmitted light emissions 176 to a detection assembly 178. Detection assembly 178 carries emission spectral filter 122 and photodetector 124. Emission spectral filter 122 is a spectral band-pass or long-pass filter used to further improve the SNR of the detection signal by blocking the undesired noise or out-of-band fluorescence signal. Optical collection device 110 operates with and without emission spectral filter 122. However, emission spectral filter 122 is employed when a higher SNR is desired.

The combination of the foregoing components of optical collection device 110 is preferably sized to provide a portable device. In this embodiment, the current size of the combination of components is about 3.5 inches (8.9 centimeters) wide, by about 5 inches (12.7 centimeters) tall.

Figure 9:
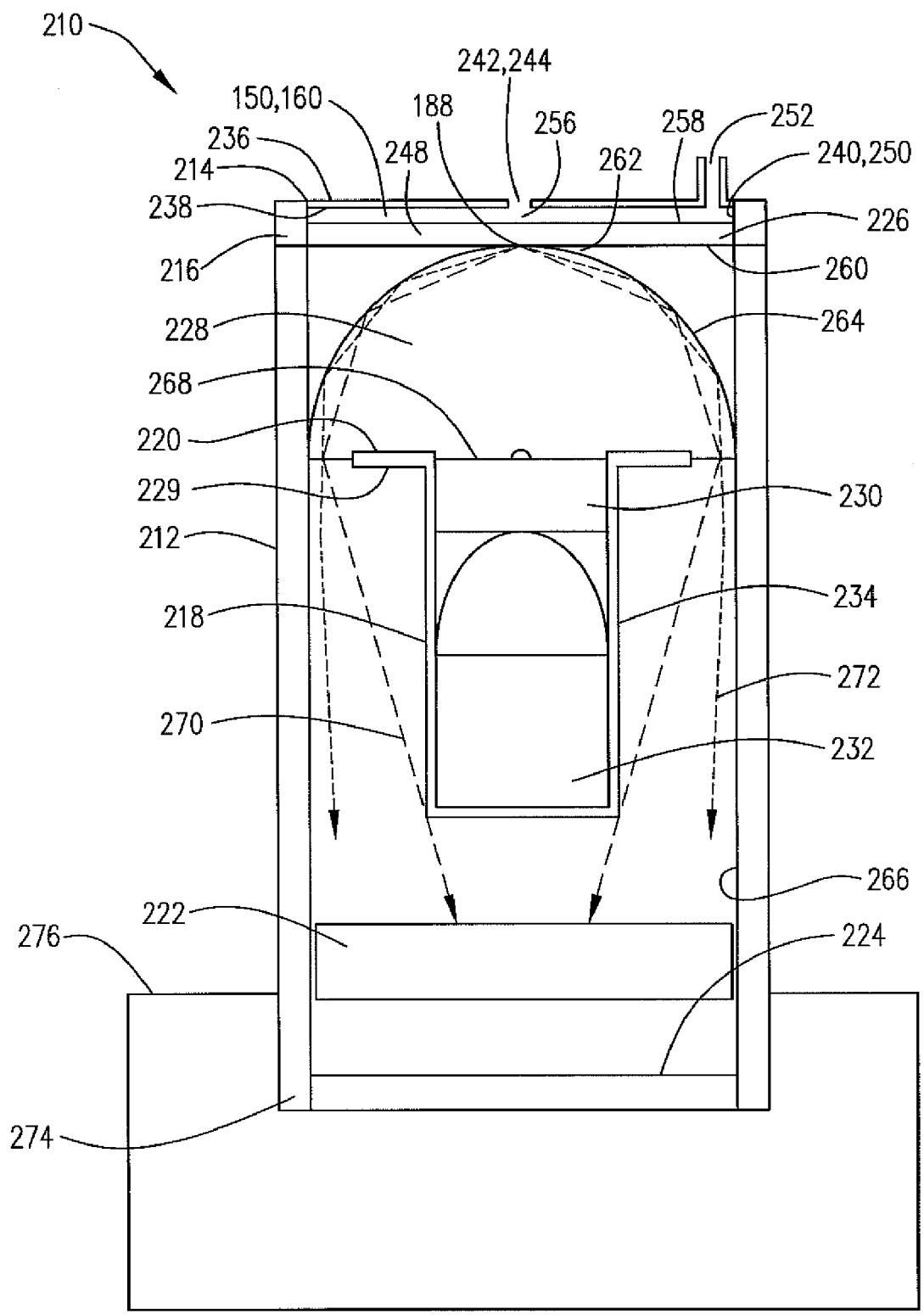
FIG. 9 schematically depicts the diagram of a miniaturized SPCE sensor arrangement sensing head.

Another embodiment illustrated in FIG. 9, provides a miniaturized optical collection device 210. In this embodiment, miniaturized optical collection device 210 comprises a housing 212. Housing 212 carries air sampling segment 216 as part of the structure. Housing 212 further carries thin disk 214, excitation assembly 218, spatial filter 220, emission spectral filter 222, and photodetector 224. Sensing slide 226 and half-ball prism lens 228 are suspended by the air sampling segment 216 and excitation assembly 218. Lens 228 may also be a half-ellipsoidal shaped prism (not shown). Excitation assembly 218 carries excitation filter 230 and light source 232, which is preferably a light emitting diode (LED). However, light source 232 may be any light source cable of generating fluorescence to include LEDs and solid-state lasers. Excitation assembly 218 is preferably contained in excitation housing 234.

Referencing FIGS. 7 and 9, air sampling segment 216 of housing 212 further comprises thin disk 214, which has first side 236 and second side 238. Thin disk 214 is preferably affixed to inner wall 240. Thin disk 214 is a thin rigid structure and has a borehole 242 in middle 244 and an exhaust port 252 near inner wall 240. Thin disk 214 and sensing slide 226 define flow channel 150. Flow channel 150 is preferably positioned across recessed area 250 of second side 238. Flow channel 150 preferably has a height of about 20 micrometers to about 100 micrometers. Flow channel 150 is in fluid communication with the first borehole 242 and exhaust port 252. Exhaust port 252 is in fluid communication with first borehole 242 and flow channel 150. In the embodiment, a small pump (not shown) creates a vacuum and draws the sampled air through first borehole 242, into flow channel 150, across sensing surface 248, and out through exhaust port 252. Flow channel 150 preferably has internal structure 158 suitable for imparting a spiraling motion to fluid flowing through flow channel 150 such that the fluid flows through sensing space 256, and across sensing slide 226 with an extended, or elongated interaction path length between the air sample and sensing slide 226. Internal structure 158, which is used to form flow channel 150, may be machined onto the surface of second side 238.

Sensing slide 226 has reacting side 258 and mounting side 260. Sensing slide 226 is affixed to half-ball prism lens 228 flattened tip 262 with an index matching fluid. By flattening the tip of half-ball prism lens 228, proper contact is made with sensing slide 226 on mounting side 260. This allows the emission from reacting side 258, on top of sensing slide 226, to be coupled into half-ball prism lens 228 with a large transmission angle due to the large SPCE angle. The emission enters into half-ball prism lens 228, and is guided by curved prism surface 264 through the "total internal reflection" and exits half-ball prism lens 228 when it reaches the cut-off facet 229 of half-ball prism lens 228. Fluorescing emission ray 270 in half-ball prism lens 228 is guided along curved prism surface 264 through a series of total internal reflections. Fluorescing emission ray 270 is then further reflected by polished reflective inner surface 266, and finally received by a photodetector 224 through an emission spectral filter 222. Preferably, half-ball prism lens 228 has an optical quality surface finish to keep the optical losses low. The surface profile does not need to be perfectly spherical as long as the local incident angle exceeds the critical angle.

Half-ball prism lens 228 is transversely positioned across housing 212, and in contact with inner wall 240. Excitation assembly 218 is held by set screws (not shown) affixed to housing 212, and pressed against the substantially flat surface 268 of the half-ball prism lens 228. Excitation housing 234 is preferably opaque, and prevents light from light source 232 to leak onto photodetector 224. Light source 232 is optically in communication with the reacting side 258 sensitized with fluorescence material on top of sensing slide 226. Light source 232 is the excitation light source that generates the optical stimulation of the fluorescence material.

Spatial filter 220 is transversely affixed to the substantially flat surface 268 of half-ball prism lens 228. Spatial filter 220 blocks a substantial portion of the remaining excitation light 272 and background light. Spatial filter 220 is configured to allow the fluorescing emission ray 270 with the desired SPCE angle to pass through with an angle of transmission (i.e. the SPCE angle) of about 70 degrees to about 85 degrees. The angle of transmission, or SPCE angle, is tuned to a range between about 70 degrees to about 85 degrees by adjusting the thickness of the second layer 46 of sensing slide 226, which is the dielectric coating layer. With such a large emission angle, the total internal reflection on the internal curved prism surface 264 of half-ball prism lens 228 is useable to guide the fluorescing emission ray 270 to photodetector 224. Spatial filter 220 is a ring shape spatial filter with an inner diameter matching the diameter of the excitation filter 230 so that excitation light 272 from excitation source 232 can penetrate through it. The outer diameter of the spatial filter 220 is smaller than the diameter of half-ball prism lens 228, so that the desired fluorescing emission ray 270, propagating along curved prism surface 264, may also penetrate it and reach the photodetector 224.

Inner wall 240 of housing 212 has reflective surface 266 sufficient to propagate fluorescing emission ray 270 to photodetector 224. Optional emission spectral filter 222 is positioned between spatial filter 220 and photodetector 224. Optional emission spectral filter 222 is used to further improve the SNR of the detection signal by blocking the undesired excitation light or the background light.

In the embodiment shown in FIG. 9, second end 274 of housing 212 is positioned in detector base 276 with a photodetector 224 positioned within inner wall 240. Housing 212 preferably has external dimensions of about 1.0 centimeters wide and about 2.5 centimeters tall.

Figure 10:
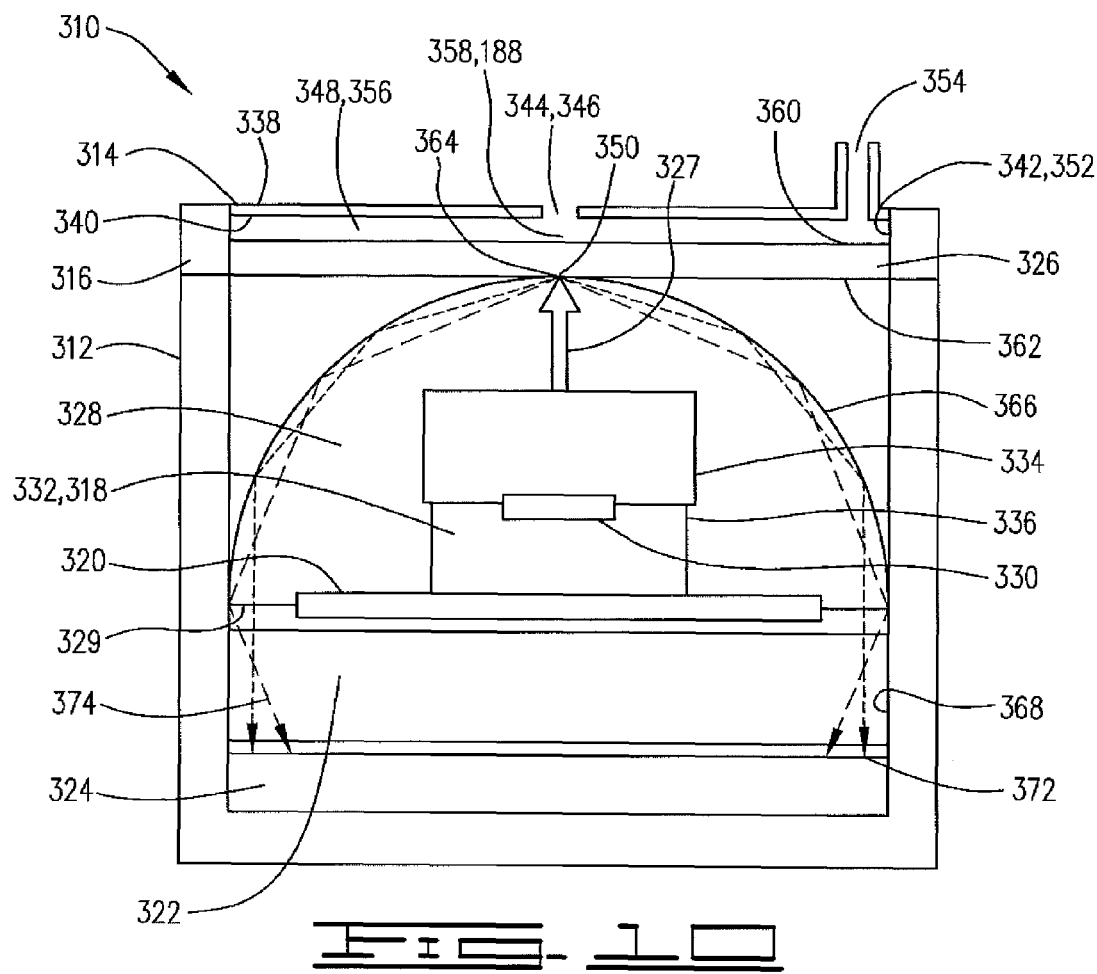
FIG. 10 schematically depicts the diagram of a compact SPCE sensor arrangement sensing head with customized optics.

Another embodiment provides a compact optical collection device as depicted in FIG. 10. The compact optical collection device 310 is contained within housing 312. Housing 312 incorporates air sampling segment 316 as part of the structure. Housing 312 also carries thin disk 314, excitation assembly 318, spatial filter 320, emission spectral filter 322, and photodetector 324. Sensing slide 326 and molded half-ball prism lens 328 are held in place by the air sampling segment 316 and excitation assembly 318. Molded half-ball prism lens 328 also carries excitation filter 330 and light source 332, which is preferably a light emitting diode (LED). However, light source 332 may be any light source cable of generating fluorescence to include LEDs and solid-state lasers. Molded half-ball prism lens 328 may also be a half-ellipsoidal shaped prism (not shown).

Referencing FIG. 10, air sampling segment 316 portion of housing 312 further comprises thin disk 314 which has first side 338 and second side 340. Thin disk 314 is preferably affixed to inner wall 342. Thin disk 314 is a thin rigid structure and has borehole 344 in middle 346 and an exhaust port 354 near inner wall 342. Thin disk 314 and sensing slide 326 define flow channel 348. Flow channel 348 is preferably disposed and positioned across recessed area 352 of second side 340. Flow channel 348 preferably has a height of about 20 micrometers to about 100 micrometers. In the embodiment, a small pump (not shown) creates a vacuum and draws the sampled air through first borehole 344, into flow channel 348, across sensing surface 350, and out through exhaust port 354. Flow channel 348 preferably has internal structure 356 suitable for imparting a spiraling motion to fluid flowing through flow channel 348 such that the fluid flows through sensing space 358, and across sensing slide 326 with an extended, or elongated, interaction path length between the air sample and sensing slide 326. Internal structure 356, which is used to form flow channel 348, may be machined onto the surface of second side 340.

In the compact optical collection device, sensing slide 326 has reacting side 360 and mounting side 362. Sensing slide 326 is affixed to molded half-ball prism lens 328 flattened tip 364 with an index matching fluid. By flattening the flatten tip 364 of molded half-ball prism lens 328, proper contact is made with sensing slide 326 on mounting side 362. This allows the emission from reacting side 360 on top of sensing slide 326, to be coupled into molded half-ball prism lens 328 with a large transmission angle due to the large SPCE angle. The emission enters in molded half-ball prism lens 328 and is guided by curved prism surface 366 through the "total internal reflection" and exits molded half-ball prism lens 328 when it reaches the cut-off facet 329 of molded half-ball prism lens 328. Fluorescing emission ray 372 in molded half-ball prism lens 328 is guided along curved prism surface 366 through a series of total internal reflections, and then further reflected by the polished inner surface 368, and finally received by a photodetector 324 through an emission spectral filter 322. Preferably, molded half-ball prism lens 328 has an optical quality surface finish to keep the optical losses low. The surface profile does not need to be perfectly spherical as long as the local incident angle exceeds the critical angle.

Molded half-ball prism lens 328 is transversely positioned across housing 312, and in contact with inner wall 342. Molded half-ball prism lens 328 is held by set screws (not shown) affixed to housing 312. Excitation filter 330, and light source 332 are preferably embedded and encapsulated within molded section 334 of molded half-ball prism lens 328. This combination may be fabricated by using customized glass for molded half-ball prism lens 328 to accommodate excitation filter 330, and light source 332, or by using customized light source 332 encapsulation process with embedded excitation filter 330 and molded half-ball prism lens 328. Light source 332 preferably has opaque substrate 336 which will prevent the light from leaking to photodetector 324. Light source 332 is optically in communication with the reacting side 360 sensitized with reporters 48 on top of sensing slide 326. Light source 332 is the excitation light source to generate the optical stimulation of the reporters 48.

Light source 332 provides first wavelength 327 to reporter 48. Reporter 48 emits a fluorescing second wavelength 372, 374. Reporter 48 is adapted to react with the analyte and create a changed second wavelength 374.

Spatial filter 320 is transversely affixed to the substantially flat surface 370 of molded half-ball prism lens 328. Spatial filter 320 blocks a substantial portion of the remaining excitation light 327 and background noise. Spatial filter 320 is configured to allow the second wavelength 372 and changed second wavelength 374 with desired SPCE angle to pass through with an angle of transmission (i.e. the SPCE angle) of about 70 degrees to about 85 degrees. The angle of transmission, or SPCE angle, is tuned to a range between about 70 degrees to about 85 degrees by adjusting the thickness of the dielectric coating layer, which is the second layer 46 of the sensing slide 326. Sensing slide 326 is similar to the sensing slide shown in FIG. 2. With such a large emission angle, the total internal reflection on the internal curved prism surface 366 of molded half-ball prism lens 328 is useable to guide the fluorescing emission ray 372 to the photodetector 324. Spatial filter 320 is a disk shaped spatial filter with its outer diameter slightly smaller than the diameter of molded half-ball prism lens 328, so that emission lights 372 and 374 from reporter 48 propagating along curved prism surface 366 may penetrate it and reach photodetector 324.

Inner wall 342 of the housing 312 has a polished inner surface 368 sufficient to propagate fluorescing emission ray 372 to photodetector 324. Optional emission spectral filter 322 is positioned between spatial filter 320 and photodetector 324. Optional emission spectral filter 322 is used to further improve the SNR of the detection signal by blocking the undesired excitation light or background light. Housing 312 preferably has external dimensions of about 1.0 centimeters wide and about 1.0 centimeters tall.

Figure 12:
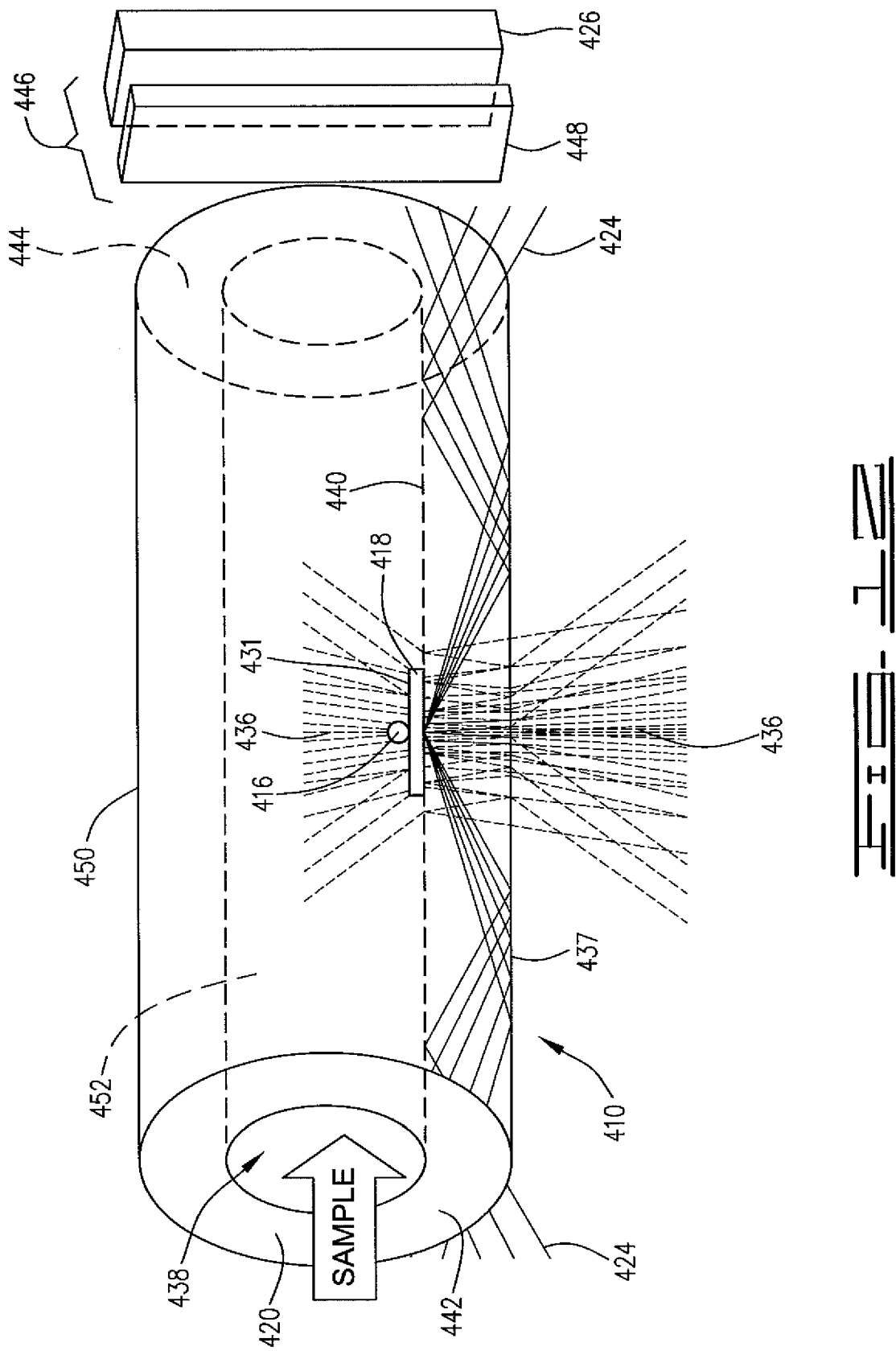
FIG. 12 depicts the SPCE collection waveguide with a capillary, thin substrate and the associated ray tracing.

In yet another embodiment, illustrated in FIG. 12, waveguiding device 410 has SPCE multilayer structure 418 coupled with waveguiding capillary structure 420. Waveguiding capillary structure 420 is a high refractive index substrate. Most of the fluorescence emitting from a thin layer of reporter 416 coated on a high refractive index substrate 420, penetrates therein and propagates within the capillary wall 437. Emission 424 is coupled through the SPCE multilayer structure 418 and propagates into capillary wall 437 as rays, or emission 424, and to detector 426.

Figure 11:
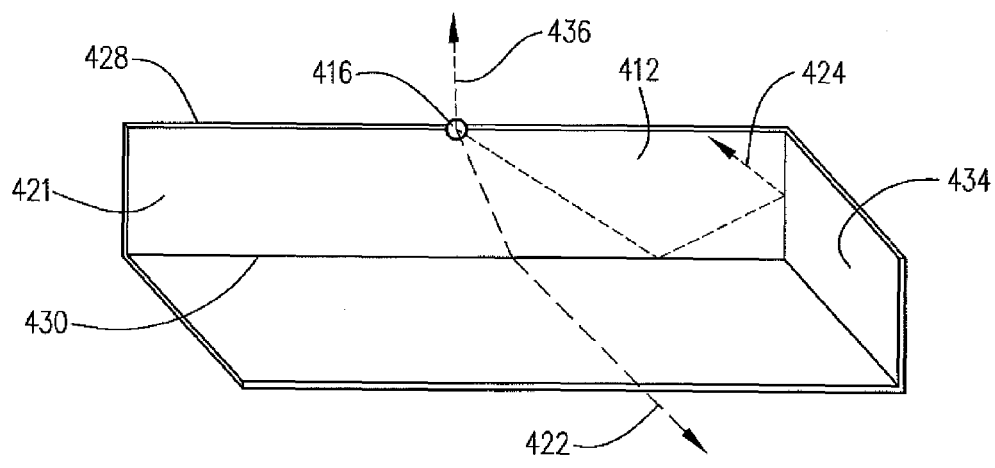
FIG. 11 schematically depicts a thin substrate with reflected and ambient light traversing therethrough.

FIG. 11 depicts an example of optical reporter 416 coated on a dielectric substrate without SPCE multilayer structure 418. In FIG. 11, reporter 416 is coated on transparent dielectric substrate 421. Most of emission 422 penetrates first surface 428 of substrate 421 with transmission angles distributed from zero degrees to the critical angle ($\theta_C$). Emission 422 entering substrate 421 with a transmission angle less than the critical angle $\theta_C$, further penetrates second surface 430 of substrate 421 if first surface 428 and second surface 430 are parallel. Therefore, such an emission will not be detected by the emission detector at the end facet 434 of substrate 421.

However, some of emission 424 entering substrate 421 with a transmission angle equal to or greater than critical angle $\theta_C$ will be bounced between first surface 428 and second surface 430 due to total internal reflection until it reaches end facet 434 of substrate 421, which is usually perpendicular to first surface 428 and second surface 430 of substrate 421. The local incident angle of emission 424 at end facet 434 is $90°-\theta_C$, which will still be greater than the critical angle $\theta_C$, if the critical angle $\theta_C$ is less than 45 degrees. This is usually the case if substrate 421 is made of a glass or an even higher refractive index material in the gaseous environment. In this case, emission 424 at end facet 434 will experience another total internal reflection and is therefore completely trapped inside substrate 421.

Referring back to FIG. 12 and as discussed herein, the SPCE fluorescing emissions have an emission peak at the deep "forbidden light" zone. The transmission angle $\theta_T$, or the SPCE angle, propagating into substrate 420 under SPCE multilayer structure 418, is greater than 45°, and hence exits end 444 towards detector 426. Since SPCE signal is a deep forbidden light, and the ambient light 436 will be rejected out of the forbidden light zone, a high SNR SPCE signal can be acquired with this configuration.

As such, an addition of waveguiding capillary structure 420 optically coupled to the aforementioned SPCE multilayer structures 418 on inner surface 440 will form a highly selective fluorescence collection device. Waveguiding capillary structure 420 is preferably an optically transparent glass capillary having a borehole 438. Waveguiding capillary structure 420 has a multilayer sensing surface 431 deposited on the inner surface 440. The first end 442 of waveguiding capillary structure 420 is facing the ambient environment, and second end 444, opposite of first end 442, is facing light detection assembly 446. Light detection assembly 446 preferably comprises spectral filter 448 and detector 426.

An excited light wave is produced when an excitation source (not shown) simulated a fluorescence material on the sensing surface. The light detection assembly 446 is at the second end 444 of waveguiding capillary structure 420 to detect the emissions. To provide air flow, a pump (not shown) is preferably connected to the borehole 438 and is adapted to pull a sufficient air sample through the borehole 438. The air sample, and/or an analyte in the air sample, interacts with reporter 416 on the multilayer sensing surface 431 of capillary structure 420.

Preferably, multilayered sensing surface 431 is a transparent substrate and a metallic thin layer capable of supporting surface plasmon resonance at the emission wavelength. Additionally, the multilayered sensing surface is a dielectric thin layer to protect the metallic layer and to position the emitter away from the metallic layer. Preferably, a fluorescence emitting material is applied to the dielectric layer. The fluorescence emitting material is reporter 416, which is preferably a reporter material for a CWIC or AFP type of material.

FIG. 12 shows the ray tracing of ambient light 436 (in dashed beams) and SPCE light emission 424 (in a solid beam) emitted by reporter 416 on top of multilayer sensing surface 431 within waveguiding capillary 420. Only the SPCE signal emission 424 can be reflected and guided effectively by capillary inner surface 440 and capillary outer surface 450, and propagated to detector assembly 446 at the second end 444 by waveguiding capillary structure 420. The ambient light 436, which is rejected out of the forbidden zone, will not be guided effectively through capillary structure 420. Therefore, as an alternative propagator for SPCE signal emission 424, waveguiding capillary structure 420 is used to achieve a very good signal-to-noise ratio.

Inner surface 440 of waveguiding capillary structure 420 is coated partially or completely with SPCE multilayer structures 418, which are thin metallic and dielectric coatings. The reactive side, or multilayer sensing surface 431, is further sensitized with a fluorescence reporter 416, which generates the SPCE signal emission 424. Borehole 438 of capillary 420 is used as flow channel 452 to deliver a gaseous sample to the sensitized reactive side, or multilayer sensing surface 431. Waveguiding capillary 420 is simultaneously used for both sample delivery and optical signal waveguiding.

III. Method

With continued reference to the drawings and the descriptions of apparatuses 10, 110, 210, 310, and 410, the current invention also provides an improved method for collecting optical emissions from reactions with explosive, chemical or biological substances. In particular, the collection method of the current invention is not limited to a laboratory, but may be carried out in a field environment such as a field of combat, airport/seaport security, sporting events, border control, and any other security point or checkpoint.

By way of example, only one of the embodiments is used to define the method for the optical collection device. The same method is applicable for the other embodiments. In the method of use, optical collection device 110 is assembled and prepared for use. After optical collection device 110 is prepared for use, and prior to operation of photodetector 124, the pump is turned on and tested to ensure operation within desired parameters. In general, small field portable pumps, which may be battery powered, are used to provide an air flow rate of about 30 cm³/min to about 1000 cm³/min. In operation, an air sample is drawn in through air sampling nozzle 116, by the pump connected to optical collection device 110 via tubing. The pump permits adjustment of the flow rate to accommodate operational conditions. Preferably, an in-line flow meter (not shown) monitors air flow through air sampling nozzle 116 and communicates with a microprocessor or other suitable device to maintain a consistent flow of air through air sampling nozzle 116 by controlling operation of the pump. During operation, the pump should also be able to heat the air sample to a temperature of about 80 degrees Celsius to about 102 degrees Celsius.

When used in the field, optical collection device 110 is operated by placing air sampling nozzle 116 in an air stream or in the vicinity of an object of interest. With the pump operating, an air sample enters air sampling nozzle 116. Based upon the field requirements, the operator adjusts the pump to control the sample flow rate to accommodate operational conditions.

The air sample is drawn in through first borehole 146, and subsequently passes over sensing slide 126. The flow channel 150 directs the air sample through internal structure 158 in a swirling method across sensing slide 126. The air sample traverses sensing slide 126 for an extended time and path length, while the explosive, chemical or biological substance, or analyte in the air sample, reacts with the fluorescence material positioned on the reactive side of sensing slide 126. Preferably, the flow rate is adjusted to allow the explosive, chemical or biological substance to interact with the fluorescence material with sufficient time, i.e. within less than 3 seconds. Additionally, the fluorescence material preferably returns to the non-reactive state in less than 60 seconds after the exposure to an explosive, chemical or biological substance has ceased.

Light source 132 emits an excitation light that optically interrogates the fluorescence material. As the fluorescing material interacts with an explosive, chemical or biological substance, the fluorescing material undergoes a change in intensity, emission spectrum, or SPCE angle of the transmitted light emission 176. As recognized by those skilled in the art, this reaction, which could be either physisorption, chemisorption, or a change in chemical structure changes the emission characteristics.

Transmitted light emission 176 propagates through ellipsoidal mirror 114, or half-ball prism lens 228 or 328, for the other embodiments. The resulting change in the light emission is detected by photodetector 124 which transmits an electrical signal to a data acquisition device (not shown) associated with or incorporated into apparatus 110.

Optional spatial filter 120, and emission spectral filter 122, eliminates unwanted light in the "forbidden light" zone as transmitted light emission 176, the fluorescing emission, propagates to photodetector 124. Detection of the change of transmitted light emission 176 by photodetector 124 positioned within optical collection device 110 signals a positive test for explosive, chemical or biological substances.

Thus, the method of the current invention does not require prior processing of an air sample to detect explosive, chemical or biological substances. Rather, the current invention permits immediate processing of air samples suspected of containing explosive, chemical or biological substances. The current invention also provides an improved and effective means to collect the optical emission from the reactive side of a SPCE slide with enhanced SNR by taking advantage of the forbidden light detection principle, spatial filtering, and spectral filtering. Accordingly, the methods and apparatus of the current invention are well suited to a field environment where rapid testing of suspected samples for trace amounts of explosive, chemical or biological substances is critical. In an alternative embodiment, sensing slide 16 is removable and replaceable in the field.

The current invention also provides a method for detecting chemical based substances within an analyte transport fluid such as air. A sample of the analyte transport fluid is taken using optical collection and detection device 10. The analyte transport fluid carries at least one target analyte.

In the preferred embodiment, light source 58 illuminates reporter 48. Light source 58 produces a wide spectrum. The wide spectrum is filtered to a first wavelength that illuminates reporter 48, thereby creating fluorescence emitting from reporter 48. The emitted fluorescence is at a second wavelength. The reporter may emit a plurality of wavelengths, each with a distinct wavelength. The plurality of wavelengths are referred to as wavelength bins. The second wavelength or second wavelength bins: are detected by detector 24.

Reporter 48 is reacted with the target analyte. The reaction occurs while reporter 48 is continuously illuminated with the first wavelength. The reaction produces a changed second wavelength, or third wavelength, that is different from the second wavelength. The reacting target analyte and reporter 48 may also emit a number of wavelength bins, each with a distinct wavelength. The changed second wavelength or changed second wavelength bins are detected by detector 24.

Alternatively, the reaction of reporter 48 with the target analyte produces a change in the intensity of the second wavelength. Since the type of fluorescence change is known for each reporter analyte pairing, detector 24 is adapted to measure the change in intensity of second wavelength or second wavelength bins, or to detect the resulting changed second wavelength or changed second wavelength bins.

Preferably, the first wavelength is filtered by first optical filter 60 and the second and changed second wavelength are filtered by second optical filter 54. The filtering process by excitation optical filter 60 and emission optical filter 54 removes a portion of the wavelength before further propagation occurs. In operation, first optical filter 60 filters out the bandwidth from first wavelength to allow only the desired wavelength to illuminate reporter 48. Second optical filter 54 filters out all of the other bandwidths except the designed bandwidth for the particular reporter 48 and a particular analyte.

In one embodiment of the method, it may be desirable to heat the analyte transport fluid. A non-limiting example of a range of temperatures for heating is about 40 degrees Celsius to about 120 degrees Celsius, Heating beyond about 120 degrees Celsius will also provide increased benefits. The heating may occur outside of air sampling nozzle 26 or a heating element may be embedded within or attached to air sampling nozzle 26. The step of heating the analyte transport fluid to a set temperature is determined by the particular reporter 48 and the particular analyte.

IV. Alternative Deployment Methods

One alternative method for determining a single analyte uses the first embodiment device 10 with a single reporter 48 and a single detector 24. This alternative provides for an increase in the performance in sensitivity of about five (5) to about eight (8) times over existing technologies. Additionally, this alternative provides for a faster response time of about two (2) times over existing technologies.

Another embodiment for discriminating analytes against a fluorescence spectrum uses the first embodiment with a single reporter 48 and an array detector 24. Using array detector 24 provides for the detection of the second and changed second wavelength bins. Comparing the intensity change between the wavelength bins, the type of target analyte can be determined, as depicted in FIGS. 17 and 18, and described below. The intensity changes among wavelength bins are correlated with a particular target analyte. It is known to those skilled in the art that fluorescence will fluctuate due to ambient temperature changes and generate unwanted optical interference.

By comparing the intensity changes among the wavelength bins, the ambient temperature effect is determined and produces at least one data point of optical interference information. The ambient temperature induced optical interference information allows for adjusting detection software to remove unwanted optical interference information.

Yet another embodiment for discriminating a plurality of analytes uses the first embodiment with a plurality of reporters 48 and an array detector 24. Using array detector 24 provides for the detection of the second and changed second wavelength bins. Comparing the intensity change between the wavelength bins, the type of target analytes can be determined by correlating the intensity changes with a particular target analyte. The addition of multiple reporters provides for the detection of multiple target analytes in a single sampling process.

V. Test Results

A test to assess the impact of temperature of the analyte transport fluid on the intensity of the reaction of the analyte and reporter was conducted using the first preferred embodiment. A TNT vapor generator (Vgen), based on the acoustic means to dispel a fixed amount of a sample, was used as the analyte for the analyte transport fluid. The Vgen sample was in vapor form and roughly in the low picogram range. The analyte transport fluid was pre-heated to a temperature between 90 degrees Celsius and 120 degrees Celsius prior to entering capillary 28. The temperature of the analyte transport fluid at sensing slide 16 was about 40 degrees Celsius due to cooling loss in capillary 28. The flow rate of the analyte transport fluid was set to about 30 milliliters per minute. C-ring 36 was made of Teflon® and about 50-75 nanometers thick. Sensing slide 16 was coated with AFP material as the reporter. The results of the test are shown in FIGS. 13-17.

The sensogram, which is the time history of the acquired fluorescence signal, is plotted in FIG. 13. The results acquired with several different temperature settings of the air sampling nozzle are compared. In FIG. 13, first trace 68 has a temperature of 97 degrees Celsius, second trace 70 has a temperature of 103 degree Celsius, and third trace 72 has a temperature of 109 degrees Celsius, Baseline trace 74 is shown and had a temperature of 90 degrees Celsius. The full width at half minimum (FWHM) were about 9.6 seconds for first trace 68, 4.6 seconds for second trace 70, and 3.6 seconds for third trace 72 compared to 5.0 seconds for baseline trace 74. A 109 degrees Celsius setting is about 30% sharper, and the SNR of the data is about six (6) times better than the baseline data.

Additionally, the data of the test suggests that reducing the size of reporter 48 will increase performance. As shown in FIG. 13, when using AFP as reporter 48, an excessively large area of reporter 48, AFP in this test, not only reduced the SNR of the sensogram, but also produced a very slow baseline return. The smallest AFP deposition used in our test was 20 nanoliters. The results for the 20 nanoliter sample show that the FWHM of the quenching curve was about 2.2 seconds, which is more than two times faster than the baseline response. The results are shown on FIG. 13 as trace 75.

A key point of using this invention is to capture a larger number of photons from the emitted wavelengths for improved signal to noise ratio. A first test used a band-pass (BP) optical filter in the first embodiment. However, emissions from the AFP through the first embodiment extended into wavelengths greater than 500 nm. A long-pass (LP) filter allows the harvesting of more photons. Using a LP filter, the total SNR is improved with a greater signal and only slightly elevated noise. The improvement by using the LP filter confirms that the SNR advantage of using this invention comes from the higher photon collection efficiency.

Testing for target discrimination using spectral analysis shows the SPCE approach is improved over standard testing. The SPCE is a highly dispersive phenomenon, which means that the emissions from different reporters at different wavelengths will be distributed at different emission angles. Therefore, SPCE emission data contains a significant amount of spectral and spatial information. FIG. 14 shows a typical AFP SPCE map with a 30 nanometer SiO2 layer between an AFP and metal layer. This map shows the angular and spectral distribution of the AFP emission. In the spectral (horizontal) axis, the two major emission peaks located at 460 and 490 nanometers can be easily identified, peak 77 and 79 respectively. The AFP SPCE has significant spectral content beyond 500 nanometers, which was not observed in non-SPCE testing. On the emission angle (vertical) axis, the 460 nanometers fluorescence peaks at about 68 degrees, and 490 nanometers at 60 degrees. With a thinner SiO2 layer, the dispersion (angular separation of different emission peaks) would be smaller.

Testing for the different quenching ratios of different explosive related analytes was also accomplished at different wavelengths. Three separate monitored emission band wavelengths are depicted in FIG. 15. First monitored emission band 76 was 465 nanometers. Second monitored emission band 78 was 495 nanometers. Third monitored emission band 80 was 515 nanometers. The tool to monitor these emission bands was the SPCE system above in conjunction with a fiber optic spectrometer. The time history plots of AFP/SPCE fluorescence signals observed at about 64 degrees emission angle at three different wavelengths are shown in FIGS. 16 and 17. The SNR of these curves were low compared to FIG. 13 because a fiber-based spectrometer was used for data collection, which can only collect very small portions of SPCE into the spectrometer.

For DNT tests shown in FIG. 16, both emission band 76 at 465 nanometers and emission band 78 at 495 nanometers have a similar quench ratio and emission band 80 at 515 nanometers has less quenching after the DNT vapor being introduced at about the $75^{th}$ second. However, both emission band 78 and emission band 80 in FIG. 17 have similar response for nitroglycerin (NG), and emission band 76 was observed to have less quenching after the NG vapor reached the sensing surface at about the $40^{th}$ second. This trend is reproducible, thereby providing explosive identification data.

It is also known that sample temperature will change the fluorescence intensity. Similar temperature induced fluorescence signal changes can be observed in both FIGS. 16 and 17. For a slow rising temperature before the $70^{th}$ second, emission band 76 at 465 nanometers showed slowly increasing intensity, emission band 80 at 515 nanometers had a reduced intensity, and emission band 78 at 495 nanometers had a similar response to emission band 80. The intensity responses were reversed to the quickly dropping temperature. Such temperature effect can be well observed after about the $120^{th}$ second when the Gas Chromatograph (GC) oven rapidly reduced its temperature at the end of the GC run. The temperature effect has much larger amplitude due to larger temperature changes. This time, a much large, but opposite effect on emission band 76 and emission band 80 can be seen. Emission band 78 again has the same rising response to emission band 80, but has less temperature sensitivity.

Computer modeling shows that multiple target discrimination using a plurality of reporters 48 in an array is easily achievable with the inventive embodiments. An array of reporters 48, such as AFP, deposited on sensing slide 16 can be less than about 1 millimeter in diameter with manual deposition. With a mechanized deposition, each reporter 48 will be as small as several hundred microns in diameter, and the total array will be less than about 1×1 millimeter squared, as shown in FIG. 4. Multiple reporters 48 such as AFP, Phenyl Quinoline, or other similar class of material, can be deposit in a tight array format within the common sample flow path to detect various explosives simultaneously. By selecting reporters 48 with different emission wavelengths, this invention can separate the emission from reporters 48 spectrally and spatially, and detect them individually with an array detector 24. Reporter 48 emissions will maintain their spatial and spectral information while propagating through device 10 to be collected by a 2D CCD array detector 24. The spectral information can then be collected and differentiated by the 2D CCD array detector 24 for target discrimination and simultaneous detections.

Other embodiments of the current invention will be apparent to those skilled in the art from a consideration of this specification or practice of the invention disclosed herein. Thus, the foregoing specification is considered merely exemplary of the current invention with the true scope thereof being defined by the following claims.

What is claimed is:

1. An optical detection device comprising:
    an input segment adapted to receive an analyte transport fluid;
    an optic segment including:
        a mirror;
        an excitation assembly, said excitation assembly including a light source emitting a first wavelength;
        a first lens optically connected to said excitation assembly;
        at least one focusing lens;
        a detector;
    a sensing slide carrying at least one reporter thereon, said reporter being selected to react with at least one target analyte, thereby producing an emission having at least a second wavelength;
    said sensing slide positioned between said input segment and said optic segment, said sensing slide being in fluid communication with said input segment and in optical communication with said optic segment, wherein said second wavelength is coupled and re-radiated in far-field radiation by said sensing slide; and
    said optical segment positioned to separate said second wavelength into at least two different wavelengths, wherein said detector is adapted to spectrally detect different wavelengths and measure an intensity of each wavelength.

2. The apparatus of claim 1, wherein said input segment, optical segment and sensing slide are disposed within a single housing.

3. The optical detection device of claim 1, wherein said light source produces a first wavelength suitable for emitting at least one wavelength in said reporter.

4. The optical detection device of claim 3, wherein said wavelength generated includes a fluorescing wavelength in said reporter.

5. The optical detection device of claim 1, wherein:
    said sensing slide has a plurality of reporters disposed thereon, each reporter adapted to react to a separate target analyte, and said light source produces at least a first wavelength suitable for generating a plurality of emission wavelengths in said plurality of reporters.

6. The optical detection device of claim 5, wherein each reporter is adapted to emit a change in an intensity of said emission wavelengths when reacting with said target analyte.

7. The optical detection device of claim 5, wherein said plurality of reporters are positioned in an array on said sensing slide, said array of reporters having a total area of about 10 millimeters squared to about 1 millimeter squared or smaller.

8. The optical detection device of claim 1, wherein said excitation assembly further comprises an optical filter, said optical filter is adapted to allow only a portion of said first wavelength to reach said reporter, said portion adapted to create fluorescing in said reporter.

9. The optical detection device of claim 1, wherein said optic segment has a first optical filter positioned within said excitation assembly and a second optical filter positioned before said detector.

10. The optical detection device of claim 1, wherein said optical segment further comprises a plurality of focusing lens.

11. The optical detection device of claim 1, wherein said sensing slide carries a plurality of layers comprising:
  a first layer comprising a metal film;
  a second layer comprising a dielectric film applied on top of said first layer; and
  a third layer comprising said reporter applied on top of said second layer.

12. The optical detection device of claim 1, wherein said input segment further comprises:
  a capillary providing fluid communication with said input segment, said capillary being adapted to stabilize said analyte transport fluid; and
  a flow cell in fluid communication with said capillary and said sensing slide.

13. The optical detection device of claim 12, wherein said input segment further comprises an air sampling nozzle with said capillary being disposed therein.

14. The optical detection device of claim 1, wherein said input segment further comprises a heating element, said heating element adapted to heat said analyte transport fluid.

15. The optical detection device of claim 1, wherein said detector is in optical communication with said optic segment and said detector is an array detector.

16. The optical detection device of claim 1, further comprising a replaceable sensing segment, said sensing segment including the sensing slide and a first lens, said sensing slide carrying at least one reporter thereon.

17. The optical detection device of claim 16, wherein said lens is a transparent dielectric cylinder.

18. The optical detection device of claim 1, wherein said sensing slide is removable.

19. The apparatus of claim 1, wherein said first lens is a prism lens.

20. The apparatus of claim 19, wherein said prism lens is a half-ball prism lens.

21. The apparatus of claim 19, wherein said prism lens is a half-ellipsoidal shaped prism lens.

22. The apparatus of claim 1, wherein said second wavelength is coupled and re-radiated via surface plasmon wave coupling effect.

23. The optical detection device of claim 1, wherein said light source produces a first wavelength suitable for generating a fluorescing wavelength in said reporter.

24. A method to detect chemical and biological based substances comprising:
  sampling an analyte transport fluid with a collection device, said analyte transport fluid carrying at least one target analyte;
  heating said analyte transport fluid;
  illuminating at least one reporter positioned in said collection device with an illuminating source at a first wavelength, whereby during illumination said reporter fluoresces at a second wavelength;
  detecting said second wavelength with a detector;
  reacting said at least one target analyte with at least one reporter while continuing to illuminate said reporter at said first wavelength thereby producing a change to said second wavelength;
  detecting said change to said second wavelength; and
  signal processing an output of said detector to determine said change to second wavelength detected, wherein said change to said second wavelength is an intensity change of said second wavelength, said intensity is correlated with at least one target analyte thereby allowing identification of said target analyte, thereby providing at least one data point on ambient temperature induced optical interference and allowing compensation for temperature changes.

25. An optical detection device comprising:
  an input segment adapted to receive an analyte transport fluid;
  an optic segment including;
    a mirror;
    an excitation assembly, the excitation assembly including a light source emitting a first wavelength;
    a first lens optically connected to the excitation assembly;
    at least one focusing lens;
  a sensing slide carrying at least one reporter thereon, the reporter being selected to react with at least one target analyte carried by the analyte transport fluid, thereby producing an emission having at least a second wavelength;
  the sensing slide positioned between the input segment and the optic segment, the sensing slide being in fluid communication with the input segment and in optical communication with the optic segment, wherein the second wavelength is coupled and re-radiated by surface plasmon wave coupling effect by the sensing slide, the sensing slide including:
    a first layer comprising a metal film capable of supporting a surface plasmon wave;
    a second layer comprising a dielectric film applied on top of the first layer;
    a third layer comprising the reporter applied on top of the second layer; and
  a detector in optical communication with the optic segment, the optical segment positioned to separate the second wavelength into at least two different wavelengths, wherein the lens is adapted to optically change and shift the second wavelength to a new optical path, and the detector is adapted to spectrally detect different wavelengths and measure an intensity of each wavelength.

* * * * *

UNITED STATES PATENT AND TRADEMARK OFFICE
CERTIFICATE OF CORRECTION

PATENT NO. : 7,982,878 B1
APPLICATION NO. : 12/245574
DATED : July 19, 2011
INVENTOR(S) : Shiou-jyh Ja It is certified that error appears in the above-identified patent and that said Letters Patent is hereby corrected as shown below:

In the specification,
In Column 1, line 16, delete "The United States Government may have rights in, and to, this application by virtue of this funding." and insert --The Government has certain rights in this invention.--

Signed and Sealed this
Twenty-sixth Day of July, 2016

Michelle K. Lee
*Director of the United States Patent and Trademark Office*